United States Patent [19]

Townsend et al.

[11] Patent Number: 5,912,356

[45] Date of Patent: *Jun. 15, 1999

[54] ANTIVIRAL NUCLEOSIDE ANALOGUES CONTAINING A SUBSTITUTED BENZIMIDAZOLE BASE ATTACHED TO A CARBOCYCLIC RING

[75] Inventors: Leroy B. Townsend, Ann Arbor, Mich.; Susan Mary Daluge, Chapel Hill, N.C.

[73] Assignees: Glaxo Wellcome Inc., N.C.; The Regents of the University of Michigan, Mich.

[ * ] Notice: This patent is subject to a terminal disclaimer.

[21] Appl. No.: 08/793,278

[22] PCT Filed: Sep. 11, 1995

[86] PCT No.: PCT/US95/11366

§ 371 Date: Apr. 7, 1997

§ 102(e) Date: Apr. 7, 1997

[87] PCT Pub. No.: WO96/07646

PCT Pub. Date: Mar. 14, 1996

Related U.S. Application Data

[63] Continuation-in-part of application No. 08/304,006, filed as application No. PCT/GB93/00479, Mar. 8, 1993, Pat. No. 5,534,535.

[51] Int. Cl.$^6$ ............... C07D 235/04; C07D 235/24; C07D 235/10

[52] U.S. Cl. ............... 548/304.4; 548/306.4; 548/307.1; 548/307.4; 548/310.4

[58] Field of Search ............... 548/304.4, 306.4, 548/307.1, 307.4, 310.4

[56] References Cited

U.S. PATENT DOCUMENTS 5,534,535  7/1996  Townsend et al. ............... 514/395

FOREIGN PATENT DOCUMENTS 9607646  3/1996  WIPO .

*Primary Examiner*—Johann Richter
*Assistant Examiner*—Ebenezer Sackey
*Attorney, Agent, or Firm*—Nixon & Vanderhye

[57] ABSTRACT

Antiviral purine nucleoside analogues contain a substituted benzimidazole base attached to a carbocyclic ring in place of the conventional sugar residue. Methods of treating herpes viral infections and pharmaceutical formulations are also described.

14 Claims, No Drawings

ANTIVIRAL NUCLEOSIDE ANALOGUES CONTAINING A SUBSTITUTED BENZIMIDAZOLE BASE ATTACHED TO A CARBOCYCLIC RING

CROSS REFERENCE TO RELATED APPLICATIONS

This application is a 35 USC 371 of PCT/US95/11366 filed Sep. 11, 1995. This application is a continuation-in-part of application Ser. No. 08/304,006 filed Sep. 9, 1994, now U.S. Pat. No. 5,534,535 which in turn is a 35 USC 371 of PCT/GB93/00479 filed Mar. 8, 1993.

The present invention relates to certain purine nucleoside analogues containing a carbocyclic ring in place of the sugar residue, pharmaceutically acceptable derivatives thereof, and their use in medical therapy, particularly for the treatment of certain viral infections.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck.

Worldwide, HBV is a viral pathogen of major consequence. It is most common in Asian countries, and prevalent in sub-Saharan Africa. The virus is etiologically associated with primary hepatocellular carcinoma and is thought to cause 80% of the world's liver cancer. In the United States more than ten thousand people are hospitalized for HBV illness each year, an average of 250 die with fulminant disease.

The United States currently contains an estimated pool of 500,000–1 million infectious carriers. Chronic active hepatitis will develop in over 25% of carriers, and often progresses to cirrhosis. It is estimated that 5000 people die from HBV-related cirrhosis each year in the USA, and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the instance of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above.

In "Viral Infections of Humans" (second edition, Ed., Evans, A. S. (1982) Plenum Publishing Corporation, New York), Chapter 12 describes in detail the etiology of viral hepatitis infections.

Of the DNA viruses, the herpes group is the source of many common viral illnesses in man. The group includes cytomegalovirus (CMV), Epstein-Barr virus (EBV), varicella zoster virus (VZV), herpes simplex virus (HSV) and human herpes virus 6 (HHV6).

In common with other herpes viruses, infection with CMV leads to a life-long association of virus and host and, following a primary infection, virus may be shed for a number of years. Clinical effects range from death and gross disease (microcephaly, hepatosplenemegaly, jaundice, mental retardation) through failure to thrive, susceptibility to chest and ear infections to a lack of any obvious ill effect. CMV infection in AIDS patients is a predominant cause of morbidity as, in 40 to 80% of the adult population, it is present in a latent form and can be reactivated in immuno-compromised patients.

EBV causes infectious mononucleosis and is also suggested as the causative agent of nasopharyngeal cancer, immunoblastic lymphoma, Burkitt's lymphoma and hairy leukoplakia.

VZV causes chicken pox and shingles. Chicken pox is the primary disease produced in a host without immunity. In young children, it is usually a mild illness characterized by a vesicular rash and fever. Shingles is the recurrent form of the disease which occurs in adults who were previously infected with varicella. The clinical manifestations of shingles include neuralgia and a vesicular skin rash that is unilateral and dermatomal in distribution. Spread of inflammation may lead to paralysis or convulsions and coma can occur if the meninges becomes affected. In immunodeficient patients, VZV may disseminate causing serious or even fatal illness.

HSV 1 and HSV 2 are some of the most common infectious agents of man. Most of these viruses are able to persist in the host's neural cells. Once infected, individuals are at risk of recurrent clinical manifestation of infection which can be both physically and psychologically distressing. HSV infection is often characterized by extensive lesions of the skin, mouth and/or genitals. Primary infections may be subclinical although they tend to be more severe than infections in individuals previously exposed to the virus. Ocular infections by HSV can lead to keratitis or cataracts. Infection in the newborn, in immunocompromised patients or penetration of infection into the central nervous system can prove fatal. HHV6 is the causative agent of roseola infantum (exanthum subitum) in children which is characterized by fever and the appearance of a rash after the fever has declined. HHV6 has also been implicated in syndromes of fever and/or rash and pneumonia or hapatitis in immunocompromised patients.

It has now been discovered that certain substituted benzimidazole compounds as referred to below, are useful for the treatment or prophylaxis of certain viral infections. According to a first aspect of the present invention, novel compounds of the formulas (I) and (I-1) are provided

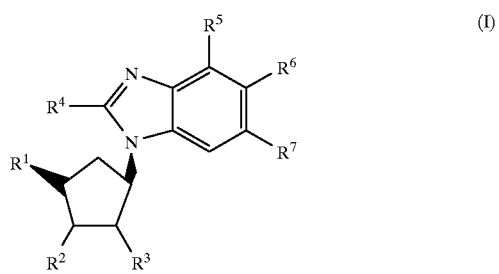

(I)

-continued

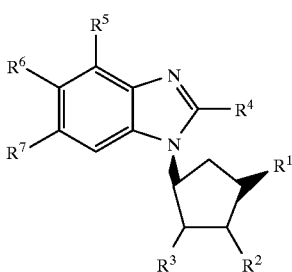
(I-1)

wherein
$R^1$ is H, $CH_3$ or $CH_2OH$; $R^2$ is H or OH; $R^3$ is H or OH; or $R^2$ and $R^3$ together form a bond;
$R^4$ is amino, cyclopropylamino, cyclobutylamino, isopropylamino, tert-butylamino or —$NR^8R^9$ where $R^8$ and $R^9$ together with the nitrogen atom to which they are attached form a 4, 5 or 6-membered heterocyclic ring; $R^5$ is H and $R^6$ and $R^7$ are Cl, excluding the compound (±)-(1R*, 2S*, 3S*, 5S*)-5-[5,6-Dichloro-2-(cyclopropylamino)-1H-benzimidazol-1-yl]-3-(hydroxyomethyl)-1,2-cyclopentanediol and provided that at least one of $R^1$, $R^2$ and $R^3$ is or contains OH;
Preferred compounds of formula (I) and (I-1) are those wherein $R^4$ is cyclopropylamino, isopropylamino or tert-butylamino and especially isopropylamino or tert-butylamino.

Preferred compounds of Formula (I) and (I-1) are those of Formula (IA) or (IA-1)

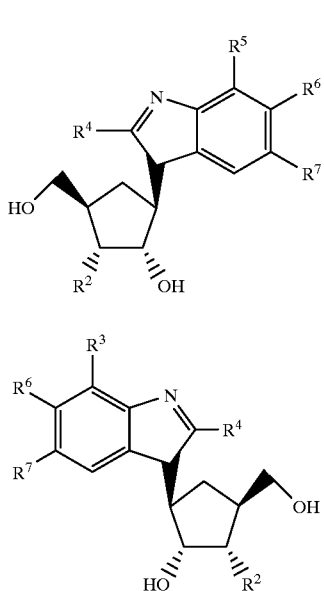

wherein $R^2$ is H or OH; $R^4$ is amino, cyclopropylamino, isopropylamino, tert-butylamino, especially isopropyl or tert-butylamino, or —$NR^8R^9$ where $R^8$ and $R^9$ together with the nitrogen atom to which they are attached form a 4, 5 or 6 membered heterocyclic ring; $R^5$ is H; and $R^6$ and $R^7$ are Cl, and excluding the compound (±)-(1R*, 2S*, 3S*, 5S*)-5-[5,6-Dichloro-2-(cyclopropylamino)-1H-benzimidazol-1-yl]-3-(hyroxyomethyl)-1,2-cyclopentanediol and pharmaceutically acceptable derivatives thereof.

Particularly preferred compounds of formula (IA) and (IA-1) are those wherein $R^4$ is cyclopropylamino, isopropylamino or tert-butylamino; $R^5$ is H; and $R^6$ and $R^7$ are both Cl; and the pharmaceutically acceptable derivatives thereof. It is to be understood that the present invention encompasses the particular enantiomers depicted in formula (I) and (I-1), including tautomers of the purine, alone and in combination with their mirror-image enantiomers. Enantiomers depicted by formula (I) are preferred and preferably are provided substantially free of the corresponding enantiomer to the extent that it is generally in admixture with less than 10% w/w, preferably less than 5% w/w, more preferably less than 2% w/w and most preferably less than 1% w/w of the corresponding enantiomer based on the total weight of the mixture. Enantiomers depicted by formula (I-1) are most preferred and preferably are provided substantially free of the corresponding enantiomer to the extent that it is generally in admixture with less than 10% w/w, preferably less than 5% w/w, more preferably less than 2% w/w and most preferably less than 1% w/w of the corresponding enantiomer based on the total weight of the mixture.

Particularly preferred examples are:
(1R, 2S, 3S, 5S)-5-[5,6-Dichloro-2-(cyclopropylamino)-1H-benzimidazol-1-yl]-3-(hydroxymethyl)- 1,2-cyclopentanediol;

(±)-(1R*, 2S*, 3S*, 5S*)-5-[5,6-Dichloro-2-(isopropylamino)-1H-benzimidazol-1-yl]-3-(hydroxymethyl)- 1,2-cyclopentanediol (1R, 2S, 3S, 5S)-5-[5,6-Dichloro-2-(isopropylamino)-1H-benzimidazol- 1 -yl]-3-(hydroxymethyl)-1,2-cyclopentanediol;

(1R, 2S, 3S, 5S)-5-[2-(tert-Butylamino)-5,6-dichloro-1H-benzimidazol-1-yl]-3-(hydroxymethyl)-1,2-cyclopentanediol; and (±)-(1R*, 2S*, 3S*, 5S*)-5-[2-(tert-Butylamino)-5,6-dichloro-1H-benzimidazol-1-yl]-3-(hydroxymethyl)-1,2-cyclopentanediol;

(1S,2R,3R,5R)-5-[5,6-Dichloro-2-(isopropylamino)-1H-benzimidazol-1-yl]-3-(hydroxymethyl)-1,2-cyclopentanediol;

(1S,2R,3R,5R)-5-[2-tert-butylamino-5,6-dichloro-1H-benzimidazol-1-yl]-3-(hydroxymethyl)-1,2-cyclopentanediol;

(±)-(1R*, 2S*, 3S*, 5S*)-5-[5,6-Dichloro-2-(1-azetidinyl)-1H-benzimidazol-1-yl]-3-(hydroxymethyl)-1,2-cyclopentanediol;

(1R, 2S, 3S, 5S)-5-[5,6-Dichloro-2-(1-azetidinyl)-1H-benzimidazol-1-yl]-(hydroxymethyl)-1,2-cyclopentanediol; and (1S, 2R, 3R, 5R)-5-[5,6-Dichloro-2-(1-azetidinyl-1H-benzimidazol-1-yl]]-3-(hydroxymethyl)-1,2-cyclopentanediol,
and pharmaceutically acceptable salts thereof.

The compounds of formulas (I) and (I-1) above and their pharmaceutically acceptable derivatives are herein referred to as the compounds according to the invention.

In a further aspect of the invention there are provided the compounds according to the invention for use in medical therapy particularly for the treatment or prophylaxis of viral infections such as herpes viral infections. To date compounds of the invention have been shown to be active against hepatitis B virus (HBV) and cytomegalovirus (CMV) infections, although early results suggest that the invention could also be active against other herpes virus infections such as EBV, VZV, HSVI and II and HHV6. The compunds of the present invention are particularly useful for the treatment or prophylaxis of CMV infections. Also disclosed is the use of the compounds of the invention in the preparation of a medicament for the treatment of viral infections.

Other viral conditions which may be treated in accordance with the invention have been discussed in the introduction hereinbefore.

In yet a further aspect of the present invention there is provided:

a) A method for the treatment or prophylaxis of a hepadnaviral infection such as hepatitis B or a herpes viral infection such as CMV which comprises treating the subject with a therapeutically effective amount of a compound according to the invention.

b) Use of a compound according to the invention in the manufacture of a medicament for the treatment or prophylaxis of any of the above-mentioned infections or conditions.

By "a pharmaceutically acceptable derivative" is meant any pharmaceutically or pharmacologically acceptable salt, ester or salt of such ester of a compound according to the invention, or any compound which, upon administration to the recipient, is capable of providing (directly or indirectly) a compound according to the invention, or an antivirally active metabolite or residue thereof.

The term heterocyclic ring means a saturated, unsaturated or partially saturated ring containing one or more heteroatoms independently selected from nitrogen oxygen and sulfur. Examples of such groups include azetidinyl, pyrrolidinyl and piperidinyl.

Preferred esters of the compounds of the invention include carboxylic acid esters in which the non-carbonyl moiety of the ester grouping is selected from straight or branched chain alkyl, e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulfonate esters such as alkyl- or aralkylsulfonyl (e.g. methanesulfonyl); amino acid esters (e.g. L-valyl or L-isoleucyl); and mono-, di- or triphosphate esters. The phosphate esters may be further esterified by, for example, a $C_{1-20}$ alcohol or reactive derivative thereof, or by a 2,3-di($C_{6-24}$)acyl glycerol.

With regard to the above-described esters, unless otherwise specified, any alkyl moiety present advantageously contains 1 to 18 carbon atoms, particularly 3 to 6 carbon atoms such as the pentanoate. Any aryl moiety present in such esters advantageously comprises a phenyl group.

Any reference to any of the above compounds also includes a reference to a pharmaceutically acceptable salt thereof.

Physiologically acceptable salts include salts of organic carboxylic acids such as acetic, lactic, tartaric, malic, isethionic, lactobionic, p-aminobenzoic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The above compounds according to the invention and their pharmaceutically acceptable derivatives may be employed in combination with other therapeutic agents for the treatment of the above infections or conditions. Examples of such further therapeutic agents include agents that are effective for the treatment of viral infections or associated conditions such as acyclic nucleosides (e.g. acyclovir), immunomodulatory agents such as thymosin, ribonucleotide reductase inhibitors such as 2-acetylpyridine 5-[(2-chloroanilino)thiocarbonyl)thiocarbonohydrazone, interferons such as α-interferon, 1-β-D-arabinofuranosyl-5-(1-propynyl)uracil, 3'-azido-3'-deoxythymidine, ribavirin and phosphonoformic acid. The component compounds of such combination therapy may be administered simultaneously, in either separate or combined formulations, or at different times, e.g. sequentially such that a combined effect is achieved.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 1.0 to 20 mg per kilogram body weight per day. (Unless otherwise indicated, all weights of active ingredient are calculated as the parent compound of formula (I); for salts or esters thereof, the weights would be increased proportionally.) The desired dose is preferably presented as two, three, four, five, six or more sub-doses administered at appropriate intervals throughout the day. These sub-doses may be administered in unit dosage forms, for example, containing 10 to 1000 mg, preferably 20 to 500 mg, and most preferably 100 to 400 mg of active ingredient per unit dosage form.

Ideally, the active ingredient should be administered to achieve peak plasma concentrations of the active compound of from about 0.025 to about 100 $\mu$M, preferably about 0.1 to 70 $\mu$M, most preferably about 0.25 to 50 $\mu$M. This may be achieved, for example, by the intravenous injection of a 0.1 to 5% solution of the active ingredient, optionally in saline, or orally administered as a bolus containing about 0.1 to about 250 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research,* 3 (6), 318 (1986).

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes the following process, depicted schematically, for the preparation of compounds of this invention

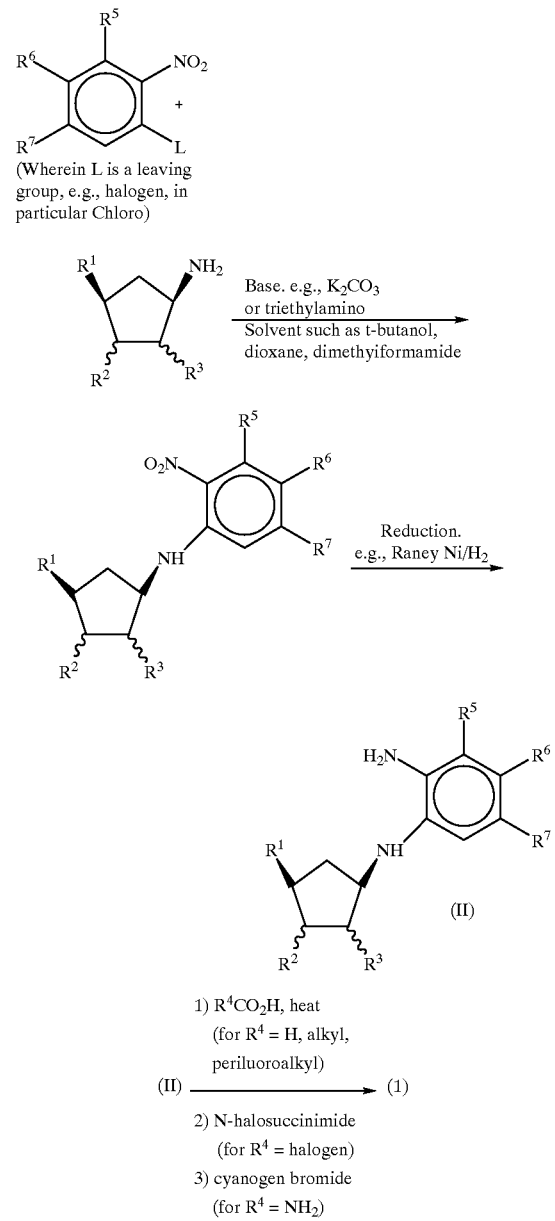

Thus, according to a further feature of the present invention we provide a process for the preparation of compounds of formulae () and (I-1) alone or in combination with their mirror image enantiomers, and their pharmaceutically acceptable derivatives which comprises (A) reacting

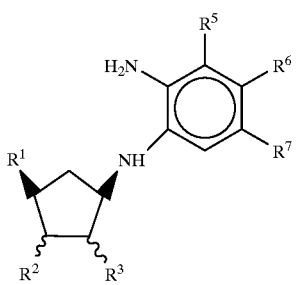

(II)

or the mirror image enantiomer thereof, with
a) either a compound of formula $R^4CO_2H$ where $R^4$ is H, $C_{1-4}$ alkyl or $C_{1-4}$ perfluoroalkyl preferably at an elevated temperature or a compound of formula $R^4C(OR)_3$ wherein $R^4$ is H, $C_{1-4}$ alkyl or $C_{1-4}$ perfluoroalkyl and R is $C_{1-4}$ alkyl, preferably at ambient temperature and in an acidic medium, to form a compound of formula (I) or (I-1) in which $R^4$ is H, or
b) cyanogen bromide to form a compound of formula (I) or (I-1) in which $R^4$ is $NH_2$; or (B)
a) converting a compound of formula (I) or (I-1) in which $R^4$ is hydrogen into a further compound of formula (1) or (I-1) in which $R^4$ is a leaving group for example by treatment with an N-(Cl, Br or I) succinimide to form a compound in which $R^4$ is Cl, or Br and
b) converting a compound of formula (I) or (I-1) in which $R^4$ is Cl, or Br into a further compound of formula (1) or (I-1) in which $R^4$ is an amino or substituted amino group —$NR^8R^9$ as defined above, by treatment with a $C_{1-4}$ alkylanine or di-$C_{1-4}$ alkylamine or $R^8R^9H$ where $R^8$ and $R^9$ are defined as above or (C) reacting a compound of formula

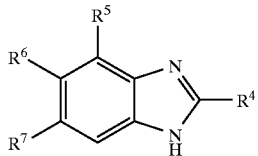

(III)

(wherein $R^4$, $R^5$, $R^6$ and $R^7$ are as herebefore defined) or a functional equivalent thereof with a compound of formula

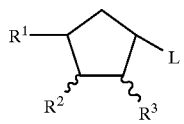

(IV)

wherein $R^1$, $R^2$ and $R^3$ are as defined above and L is a leaving group, for example an organosulphonyloxy (e.g. p-toluenesulphonyloxy or methanesulphonyloxy), halogen or triflate ($OSO_2CF_3$) group), for example in the presence of a base such as sodium carbonate or sodium hydride in a solvent such as dimethylformamide, advantageously at an elevated temperature e.g. 80–100° C., to form a compound of formula (I) or (I-1) in which $R^4$ is hydrogen, halogen or $NR^8R^9$; and optionally converting a compound of formula (a) or (I-1) into a pharmaceutically acceptable derivative thereof.

Alternatively in process (C) above the compound of formula (IV) may be replaced with a compound in which the L and $R^3$ groups are replaced with a cyclic sulphate group.

All of the structures shown above are intended to represent the enantiomers depicted as well as their mirror image isomers, as well as mixtures thereof. Thus, the present invention is intended to encompass both the racemates and the pure enantiomers, substantially free of their mirror-image isomers.

A compound of formula (I) or (I-1) may be converted into a pharmaceutically acceptable ester by reaction with an appropriate esterifying agent, e.g. an acid halide or anhydride. The compound of formula (I) or (I-1) including esters thereof, may be converted into pharmaceutically acceptable salts thereof in conventional manner, e.g. by treatment with an appropriate acid. An ester or salt of an ester of formula (I) or (I-1) may be converted into the parent compound, e.g. by hydrolysis.

The following Examples are intended for illustration only and are not intended to limit the scope of the invention in any way. The term 'active ingredient' as used in the examples means a compound of formula (I) or (I-1) or a pharmaceutically acceptable derivative thereof.

EXAMPLE A

Tablet Formulations

The following formulations A and B were prepared by wet granulation of the ingredients with a solution of povidone, followed by addition of magnesium stearate and compression.

| | Formulation A | | |
|---|---|---|---|
| | | mg tablet | mg/tablet |
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
| | | 500 | 300 |

| | Formulation B | | |
|---|---|---|---|
| | | mg tablet | mg/tablet |
| (a) | Active ingredient | 250 | 250 |
| (b) | Lactose | 150 | — |
| (c) | Avicel PH 101 | 60 | 26 |
| (d) | Povidone B.P. | 15 | 9 |
| (e) | Sodium Starch Glycollate | 20 | 12 |
| (f) | Magnesium Stearate | 5 | 3 |
| | | 500 | 300 |

| Formulation C | |
|---|---|
| | mg/tablet |
| Active ingredient | 100 |
| Lactose 200 | |
| Starch | 50 |
| Povidone | 5 |
| Magnesium stearate | 4 |
| | 359 |

The following formulations, D and E, were prepared by direct compression of the admixed ingredients. The lactose used in formulation E was of the direct compression type (Dairy Crest—"Zeparox").

|  | mg/tablet |
| --- | --- |
| Formulation D | |
| Active Ingredient | 250 |
| Pregelatinised Starch NF15 | 150 |
| | 400 |
| Formulation E | |
| Active Ingredient | 250 |
| Lactose 156 | |
| Avicel | 100 |
| | 500 |

Formulation F (Controlled Release Formulation)

The formulation was prepared by wet granulation of the ingredients (below) with a solution of povidone followed by the addition of magnesium stearate and compression.

|  |  | mg/tablet |
| --- | --- | --- |
| (a) | Active Ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

EXAMPLE B

Capsule Formulations

Formulation A

A capsule formulation was prepared by admixing the ingredients of Formulation D in Example 1 above and filling into a two-part hard gelatin capsule. Formulation B (infra) was prepared in a similar manner.

Formulation B

|  |  | mg/capsule |
| --- | --- | --- |
| (a) | Active ingredient | 250 |
| (b) | Lactose B.P. | 143 |
| (c) | Sodium Starch Glycollate | 25 |
| (d) | Magnesium Stearate | 2 |
| | | 420 |

Formulation C

|  |  | mg/capsule |
| --- | --- | --- |
| (a) | Active ingredient | 250 |
| (b) | Macrogol 4000 BP | 350 |
| | | 600 |

Capsules were prepared by melting the macrogol 4000 BP, dispersing the active ingredient in the melt and filling the melt into a two-part hard gelatin capsule.

Formulation D

|  | mg/capsule |
| --- | --- |
| Active ingredient | 250 |
| Lecithin | 100 |
| Arachis Oil | 100 |
| | 450 |

Capsules were prepared by dispersing the active ingredient in the lecithin and arachis oil and filling the dispersion into soft, elastic gelatin capsules.

Formulation E (Controlled Release Capsule)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

|  |  | mg/capsule |
| --- | --- | --- |
| (a) | Active Ingredient | 250 |
| (b) | Microcrystalline Cellulose | 125 |
| (c) | Lactose BP | 125 |
| (d) | Ethyl Cellulose | 13 |
| | | 513 |

EXAMPLE C

Injectable Formulation

Formulation A.

| | |
| --- | --- |
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient was dissolved in most of the water (35°–40° C.) and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealed with sterile closures and overseals.

Formulation B

| | |
| --- | --- |
| Active ingredient | 0.125 g |
| Sterile, pyrogen-free, pH 7 phosphate buffer, | q.s. to 25 ml |

EXAMPLE D

Intramuscular injection

| | |
| --- | --- |
| Active Ingredient | 0.20 g |
| Benzyl Alcohol | 0.10 g |
| Glycofurol | 1.45 g |
| Water for Injection | q.s. to 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE E

| Syrup | |
|---|---|
| Active ingredient | 0.2500 g |
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water | q.s. to 5.0000 ml |

The active ingredient was dissolved in a mixture of the glycerol and most of the purified water. An aqueous solution of the sodium benzoate was then added to the solution, followed by addition of the sorbitol solution and finally the flavour. The volume was made up with purified water and mixed well.

EXAMPLE F

Suppository

| Suppository | mg/suppository |
|---|---|
| Active Ingredient (631 m)* | 250 |
| Hard Fat, BP (Witepsol H15 - Dynamit Nobel) | 1770 |
| | 2020 |

*The active ingredient was used as a powder wherein at least 90% of the particles were of 631 m diameter or less.

One-fifth of the Witepsol H15 was melted in a steam-jacketed pan at 45° C. maximum. The active ingredient was sifted through a 2001 m sieve and added to the molten base with mixing, using a silverson fitted with a cutting head, until a smooth dispersion was achieved. Maintaining the mixture at 45° C., the remaining Witepsol H15 was added to the suspension and stirred to ensure a homogeneous mix. The entire suspension was passed through a 2501 m stainless steel screen and, with continuous stirring, was allowed to cool to 40° C. At a temperature of 38° C. to 40° C., 2.02 g of the mixture was filled into suitable, 2 ml plastic moulds. The suppositories were allowed to cool to room temperature.

EXAMPLE G

| Pessaries | mg/pessary |
|---|---|
| Active ingredient (631 m) | 250 |
| Anhydrate Dextrose | 380 |
| Potato Starch | 363 |
| Magnesium Stearate | 7 |
| | 1000 |

The above ingredients were mixed directly and pessaries prepared by direct compression of the resulting mixture.

Antiviral Testing

1. Anti-HCMV

Human cytomegalovirus (HCMV) is assayed in monolayers of MRC5 cells (human embryonic lung) in multiwell trays. Activity of compounds is determined in the plaque reduction assay, in which a cell monolayer is infected with a suspension of HCMV. A range of concentrations of the compound to be tested (of known molarity) is then incorporated into the carboxymethyl cellulose overlay. Plaque numbers of each concentration are expressed as percentage of the control and a dose-response curve is drawn. From this curve the 50% inhibitory concentration ($IC_{50}$) is estimated.

| Compound | $IC_{50}$ ($\mu M$) |
|---|---|
| Ex. 4 | 1.9 |

2. Anti-HBV a. Overview:

Anti-HBV activity of compounds of formula (I) and (I-1) was determined with a high-capacity assay for assessing efficacy. Supernatants from growing HBV-producing cells (HepG2 2.2.15, P5A cell line) in 96-well plates are applied to microtiter plate wells which have been coated with a specific monoclonal antibody to HBV surface antigen (HBsAg). Virus particles present in the supernatants bind to the antibody and remain immobilized while other debris is removed by washing. These virus particles are then denatured to release HBV DNA strands which are subsequently amplified by the polymerase chain reaction and detected with a calorimetric hybrid-capture assay. Quantitation is achieved through fitting of a standard curve to dilutions of a cell supernatant with known HBV DNA content. By comparing HBV DNA levels of untreated control cell supernatants with supernatants containing a compound of formula (I) or (I-1), a measure of anti-HBV effectiveness is obtained.

b. Immunoaffinity Capture of HBV:

HBV producer cells, 2500 cells/well, were seeded in 96-well culture dishes in RPMI/10% fetal bovine serum/2 mM glutamine (RPMI/10/2:). Media were replenished on days 1, 3, 5, and 7 with dilutions of a compound of formula (1) or (I-1) in RPMI/10/2 to a final volume of 150 uL. Fifty uL of mouse monoclonal anti-HBsAG antibody (10 ug/mL in PBS) were added to each well of a round-bottom microtiter plate. After incubation overnight at 4° C., the solutions were aspirated and replaced with 100 uL of 0.1% BSA in PBS. Samples were incubated for 2 hours at 37° C. and washed three times with PB S/0/01% Tween-20 (PBS/T) using a Nunc Washer. Ten uL of 0.035% Tween 20 in PBS were then added to all wells by Pro/Pette. Cell supernatants (25 uL) containing extracellular virion DNA were transferred into wells by Pro/Pette; the final Tween concentration is 0.01%. Twenty-five uL HBV standard media dilutions in RPMI/10/2 were added to 2 rows of wells to serve as an internal standard curve for quantitation, and the plates were sealed and incubated at 4° C. overnight. Samples were washed 5 times with PBS/T and 2 times with PBS, aspirating the last wash. Next, 25 uL of 0.09N NaOH/0.01% NP40 were added to each well by Pro/Pette, and the sample wells were sealed and incubated at 37° C. for 60 minutes. Samples were then neutralized with 25 uL of 0.09N HCl/100 mM tris (pH 8.3).

c. Polymerase Chain Reaction (PCR):

Polymerase chain reaction (Saiki, R. K. et al., Science, 239 (4839) 487–91 (1988)) was carried out on 5 uL samples, using a Perkin Elmer PCR kit. PCR is performed in "MicroAmp tubes" in a final volume of 25 uL. Primers were chosen from conserved regions in the HBV genome, as determined by alignment of several sequences. One primer is biotinylated at the 5-prime end to facilitate hybrid-capture detection of the PCR products. All primers were purchased from Synthecell Corp., Rockville, Md. 20850.

d. Hybrid-Capture Detection of PCR Products:

PCR products were detected with horse radish peroxidase-labeled oligonucleotide probes (Synthecell Corp., Rockville, Md. 20850), which hybridize to biotinylated strands of denatured PCR products directly in streptavidin-coated microtiter plate wells, using essentially the method of Holodiniy, M. et al., *BioTechniques*, 12 (1) 37–39 (1992). Modifications included the use of 251 PCR reaction volumes and sodium hydroxide denaturation instead of heat. Simultaneous binding of the biotin moiety to the plate-bound streptavidin during the hybridization serves to "capture" the hybrids. Unbound labeled probes were washed away before calorimetric determination of the bound (hybridized) horse radish peroxidase. Quantities of HBV DNA present in the original samples were calculated by comparison with standards. These values were then compared to those from untreated cell cultures to determine the extent of anti-HBV activity.

$IC_{50}$ (the median inhibitory concentration) is the amount of compound which produces a 50 percent decrease in HBV DNA. The approximate IC50 of the compounds of Examples 4, 13 and 69 are tabulated.

| Compound | $IC_{50}$ (μM) |
| --- | --- |
| Ex. 4 | 0.74, 2.5 |
| Ex. 32 | 1.3, 0.79 |
| Ex. 33 | 0.44, 0.50 |
| Ex. 40 | 2.0, 1.4 |
| Ex. 41 | 0.4, 0.40 |
| ganciclovir (control) | 1.1 (average of 10 values) |

EXAMPLE 1

(±)-(1R*,2S*,3S*,5S*)-3-(Acetoxmethyl)-5-(4,5-dichloro-2-nitroanilino)-1,2-cyclopentanediyl diacetate (±)-(1R*, 2S*, 3R*, 4R*)-tert-Butyl N-[2,3-dihydroxy-4-hydroxymethyl) -1-cyclopentyl]carbamate (6.27 g, 25.1 mmol) and 1N hydrochloric acid (50 mL) were stirred overnight. The resulting clear solution was concentrated in vacuo and dried by evaporation of methanol and ethanol to give the hydrochloride of (±)-(1S*, 2R*, 3S*, 5R*)-3-amino-5-(hydroxymethyl)-1,2-cyclopentanediol as a solid foam (4.73 g). This solid foam was refluxed vigorously with triethylamine (7.5 g, 75 mmol), 1,2,4-trichloro-5-nitrobenzene (5.84 g, 25.0 mmol as 97%, Aldrich), and 2-methoxyethanol (75 mL) for 24 hours. The resulting black mixture was evaporated to dryness and the residue chromatographed on silica gel and product eluted with methanol:chloroform/1:10 as a dark orange glass (6.9 g). Crystallization from ethanol-water gave orange powder (3.00 g) which was stirred in acetic anhydride (3.0 mL)—pyridine (20 mL) at ambient temperature overnight. Evaporation of volatiles, followed by crystallization from ethyl acetate-hexanes gave title compound as orange needles (2.82 g, 24%), m.p. 153–156° C.; $^1$H-NMR (DMSO-$d_6$) δ: 8.25 and 7.51 (both s, 1 each, $C_6H_2$), 8.07 (d, J=7.8 Hz, 1, NH), 5.23 and 5.09 (both m, 2, 2 CHO), 4.3 (m, 1, CHN), 4.2–4.0 (m, 2, $CH_2O$), 2.5–2.35 (m, 2, 2CH), 2.04, 2.03, 2.02 (all s, 9, $3CH_3CO$), 1.5–1.4 (m, 1, CH).

Anal. Calcd. for $C_{15}H_2ON_2O_5Cl_2$: C, 46.67; H, 4.35; N, 6.05; Cl, 15.31. Found: C, 46.66; H, 4.37; N, 6.02; Cl, 15.38.

EXAMPLE 2

(±)-(1R*, 2S*, 3 S*, 5S*)-3-(Acetoxymethyl)-5-(5,6-dichloro-1H-benzimidazol -1-yl)-1,2-cyclopentanediyl diacetate (±)-(1R*, 2S*, 3S*, 5S* )-3-(Acetoxymethyl)-5-(4,5-dichloro-2-nitroanilino) -1,2-cyclopentanediyl diacetate (2.75 g, 5.93 mmol) and Raney nickel (aqueous slurry, Aldrich, 300 mg wet) in isopropanol (250 mL) was shaken under hydrogen (40 psi) in a Parr shaker for 2.25 hours. Catalyst was filtered off with Celite and the filtrate acidified with 98% formic acid (5 mL) and concentrated to an orange oil. The oil was diluted with additional 98% formic acid (45 mL) and the resulting orange solution refluxed for 40 minutes. Volatiles were removed and the remaining dark oil dissolved in chloroform (100 mL). The chloroform solution was washed with saturated aqueous sodium bicarbonate (3×10 mL), dried (sodium sulfate), and evaporated to a foam which was chromatographed on silica gel. Title compound eluted with methanol:chloroform/3:97 as a white foam from ethyl acetate (2.26 g, 86%); $^1$H-NMR (DMSO-$d_6$) δ: 8.57, 8.17, 7.97 (all s, 1 each, 3 benzimidazole CH), 5.6 (m, 1, CHO), 5.3–5.1 (m, 2, CHO and CHN), 4.35–4.15 (m, 2, $CH_2O$), 2.6–2.4 (m overlapping solvent, 2 CH), 2.10, 2.06, 1.92 (all s) overlapped by 2.0 (m, total 10, $3CH_3CO$ and CH).

Anal. Calcd. for $C_{19}H_2ON_2O_6Cl_2$: C, 51.49; H, 4.55; N, 6.32; Cl, 16.00. Found: C, 51.39; H, 4.58; N, 6.22; Cl, 16.07.

EXAMPLE 3

(±)-(1R*, 2S*, 3S*, 5S*)-3-(Acetoxymethyl)-5-(2-bromo-5, 6-dichloro-1H-benzimidazol-1-yl)-1,2-cyclopentanediyl diacetate (±)-(1R*, 2S*, 3S*, 5S*)-3-(Acetoxymethyl)-5-(5,6-dichloro-1H-benzimidazol-1-yl)-1,2-cyclopentanediyl diacetate (1.32 g, 2.98 mmol) in dry N, N-dimethylformamide (6 mL) was heated to 60° C. Portions (ca. 1 mmol each) of N-bromosuccinimide (1.59 g, 8.93 mmol) were added over 5 hours. Heating was continued for an additional 4 hours. Volatiles were removed in vacuo and the residue chromatographed on silica gel. Title compound eluted with 1:1 hexane-ethylacetate as a tan powder (1.1 g, 69%), $^1$H-NMR identical with recrystallized sample. Such a sample was recrystallized from ethanol-water to a white powder, m.p. 156–159° C.; $^1$H-NMR (DMSO-$d_6$) δ: 8.34, 7.97 (both s, 1 each, 2 benzimidazole CH), 5.6 (m, 1, OCH), 5.3 (m, 1, OCH), 5.2–5.0 (m, 1, NCH), 4.4–4.2 (m, 2, $OCH_2$), 2.7–2.5 (m, 1, CH), 2.4–2.0 (m) overlapping 2.1 and 2.07 (both s, total 8, $CH_2$ and $2CH_3CO$), 1.92 (s, 3, $CH_3CO$); mass spectrum (CI): 527 (6.6), 525 (45), 523 (100), 521 (65, M+1), 257 (48, M-B).

Anal. Calcd. for C19H19N$_2$O$_6$ BrCl$_2$: C, 43.71; H, 3.67; N, 5.37; total halogen as Br, 45.91. Found: C, 43.64; H, 3.63; N, 5.30; total halogen as Br, 45.77.

EXAMPLE 4

(±)-(1R*, 2S*, 3S*, 5S*)-5-(2-Bromo-5,6-dichloro-1H-benzimidazol-1yl)-3-(hydroxymethyl)-1,2-cyclopentanediol (±)-(1R*, 2S*, 3S*, 5S*)-3-(Acetoxymethyl)-5-(2-bromo-5,6-dichloro-1H-benzimidazol-1-yl)-1,2-cyclopentanediyl diacetate (600 mg, 1.15 mmol) was added to a stirred mixture of sodium carbonate (122 mg) in water (2 mL)-ethanol (10 mL)-methanol (10 mL). After 2.5 hours at ambient temperature, the pH was adjusted to 7 with glacial acetic acid. Volatiles were removed in vacuo and the residue triturated with water (5 mL) and filtered to give white solid. Recrystallization of the solid from 1:1 ethanol-methanol gave title compound as a white powder (282 mg, 62%), m.p. 208–211° C.; $^1$H-NMR (DMSO-d$_6$)δ: 8.23, (s, 1, benzimidazole H7), 7.95 (s, benzimidsazole H4), 5.13 (t, J=4.1 Hz, 1, CH$_2$OH, 5.03 (d, J=6.2 Hz, 1, OH), 5.0–4.85 (m, 1, H5), 4.71 (d, J=3.5 Hz, 1, OH), 4.55–4.45 (m, 1, H1), 3.85–3.80 (m, 1, H2), 3.7–3.6 and 3.55–3.45 (both m, 1 each, OCH$_2$), 2.2–1.95 (m, 3, H3 and 2H4); mass spectrum (CI): 395 (M+1).

Anal. Calcd. for $C_{13}H_{13}N_2O_3Cl_2Br$: C, 39.43; H, 3.31; N, 7.07; total halogen as Br, 60.52. Found: C, 39.50; H, 3.33; N, 7.02; total halogen as Br, 60.61.

EXAMPLE 5

(1α, 3β)-(3,4)-Dihydroxy-1 -cyclopentyl) methyl benzoate

To a stirred, cooled (0° C.) solution of 4-hydroxymethylcyclopentene (J.-P. Depres and A. E. Green, *J. Org. Chem.* 1984, 49, 928–931, and references therein) (37.0 g, 276 mmol) in pyridine (450 mL) was added benzoylchloride (32.1 mL, 276 mmol) over 30 minutes. The resulting mixture was stirred at room temperature for 1.25 hours. Water (50 mL) was added and the volatiles removed in vacuo. The residual oil was dissolved in chloroform and the solution extracted with water and then dried over sodium sulfate. Evaporation of solvent gave (3-cyclopenten-1-yl) methylbenzoate as a yellow oil (53.94 g, 91%), sufficiently pure for use; $^1$H-NMR (DMSO-d$_6$) δ: 7.98, 7.67, 7.56 (m, 5, $C_6H_5$), 5.72 (s, 2, CH=CH), 4.19 (m, 2, OCH2), 2.71 (m, 1, CH), 2.56–2.77 (m, overlapping solvent, 2CH), 2.21–2.14 (mn, 2, 2CH).

(3-Cyclopenten-1-yl)methyl benzoate (37.6 g, 0.161 mol) in acetone (200 mL) was added dropwise over 2 hours to a stirred solution of N-methylmorpholine-N-oxide (33.1 g, 60% in water, 0.169 mol), osmium tetroxide (2.5% in t-butanol, Aldrich, 3.0 mL), and acetone (200 mL) at ambient temperature. Stirring was continued for an additional 16 hours. Chloroform (500 mL) and water (150 mL) were added. The organic layer was separated, washed with cold 1N hydrochloric acid (2×150 mL) and then with saturated aqueous sodium bicarbonate (100 mL) and dried (MgSO$_4$). Volatiles were removed and the residual solid crystallized from toluene (200 mL) to give title compound as white crystals (26.9 g, 73%), m.p. 92–94° C.; $^1$H-NMR (DMSO-d$_6$) δ: 7.96, 7.65, 7.56 (m, 5, C6H5), 4.38 (d, J=4.1 Hz, 2, 2OH), 4.14 (d, J=6.6 Hz, 2, CH$_2$O), 3.90 (m, 2, 2 OCH), 2.58 (m overlapping solvent, CH), 1.75 (m, 2, 2CH), 1.55 (m, 2, 2CH).

Anal. Calcd. for $C_{13}H_{16}O_4$: C, 66.09; H, 6.83. Found: C, 66.19; H, 6.86.

Concentration of mother liquors yielded 10.33 g of white solid which contained additional title compound contaminated by (±)-(1__, 3__, 4__-(3,4-dihydroxy-1-cyclopentyl) methyl benzoate, ratio approximately 2:3 by $^1$H-NMR.

EXAMPLE 6

(3a-α, 5α, 6a-α)-(Tetrahydro-4H-cyclopenta-1,3-2-dioxathiol-5-yl)methyl benzoate S-oxide Thionyl chloride (6.04 g, 50.8 mmol) was added to a solution of (1β, 3a, 4a)-(3,4-dihydroxy-1-cyclopentyl) methyl benzoate (10.0 g, 42.3 mmol) in carbon tetrachloride (150 mL). The solution was refluxed for 1.5 hours. Solvent was evaporated to leave title compound as a thick oil sufficiently pure for use (see following example). Such a sample crystallized as a waxy solid from toluene, m.p. 48–57° C.; $^1$H-NMR (DMSO-d$_6$)δ: 7.96, 7.66, 7.52 (m, 5, $C_6H_5$), 5.46 and 5.32 (both m, 1, 2 OCH, due to ca 1:1 mixture of isomeric S-oxides), 4.28 (m, 2, OCH$_2$), 2.90 and 2.43 (both m, 1, CH of two isomeric S-oxides), 2.10 and 1.74 (both m, 4, 4CH).

Anal. Calcd. for $C_{13}H_{14}O_5S$: C, 55.31; H, 5.00; S, 11.36. Found: C, 55.41; H, 5.04; S, 11.30.

EXAMPLE 7

(3a-α, 5α, 6a-α)-(Tetrahydro-4H-cyclopenta-1,3-2-dioxathiol-5-yl)methyl benzoate S, S-dioxide (3a-α, 5α, 6a-α-(Tetrahydro-4H-cyclopenta-1,3,2-dioxathiol-5-yl)methyl benzoate S-oxide (previous example, 42.3 mmol) was stirred in carbon tetrachloride (40 mL)-acetonitrile (40 mL)-water (60 mL) while sodium metaperiodate (8.98 g, 42.3 meq) and ruthenium trichloride (44 mg, 0.21 meq) were added. Additional sodium metaperiodate (179 mg) was added after 30 minutes to bring the reaction to completion as judged by TLC (silica gel, methanol:chloroform/1:19, visualized in iodine). After a total of 1.0 hour, methylene chloride (300 mL) was added. The organic layer was separated and the aqueous layer extracted with additional methylene chloride (300 mL). The combined organic layers were washed with saturated aqueous sodium bicarbonate (100 mL), then saturated aqueous sodium chloride (100 mL), dried (MgSO$_4$) and concentrated in vacuo to give title compound as white powder (12.37 g, 98%), m.p. 114–119° C.; $^1$H-NMR (DMSO-d$_6$)δ: 8.02, 7.70, 7.55 (all m, 5, $C_6H_5$), 5.62 (m, 2, OCH), 4.34 (d, J=5.8 Hz, 2, OCH2), 2.79–2.64 (m, 1, CH), 2.32–2.21 and 1.97–1.79 (m, 4,2 CH$_2$).

Anal. Calcd. for $C_{13}H_{14}SO_6$: C, 52.35; H, 4.73; S, 10.75. Found: C, 52.32; H, 4.73; S, 10.69.

EXAMPLE 8

(±)-(1R*, 2R*, 4S*)-2-(5,6-Dichloro-1H-benzimidazol-1-yl)-4-(hydroxymethyl) cyclopentanol Sodium hydride (416 mg, 10.4 meq as 60% oil dispersion) was added to a solution of 5,6-dichlorobenzinidazole (L. B. Townsend and G. R. Revankar, *Chem.Rev.* 1970, 70, 389, and references therein) (1.50 g, 8.00 mmol) in dry N,N-dimethylformamide (35 mL). The mixture was stirred for 45 minutes at 25° C. (3a-α, 5α, 6a-α-(tetrahydro-4H-cyclopenta- 1,3–2-dioxathiol-5-yl)methyl benzoate S, S-dioxide (3.05 g, 10.2 mmol) (prepared in Examples 7, 8 and 9) was added in portions over 5 hours. Stirring was continued overnight at ambient temperature. Volatiles were removed in vacuo and the residual oil dissolved in 1,4-dioxane (130 mL)-water (10 mL) at reflux with 4M sulfuric acid (2.3 mL). After 10 minutes at reflux, the solution was basified with 5N sodium hydroxide, heated for an additional hour at 50° C., and then neutralized with additional acid. Evaporation of volatiles in vacuo gave residual solids which were extracted with chloroform to remove unreacted 5,6-dichlorobenzimidazole and then crystallized from ethanol-water to give title compound as white powder (2.09 g, 87%). Recrystallization of such a sample from ethanol-water gave title compound as white granules, m.p. 244–245° C.; $^1$H-NMR (DMSO-d$_6$) δ: 8.47, 8.05, 7.93 (all s, 3, aryl CH), 5.19 (d, J=5.3 Hz, 1, CHOH), 4.71 (t, J=5.3 Hz, 1, CH$_2$OH), 4.6–4.5 (m, 1, NCH), 4.37–4.25 (m, 1, OCH), 3.41 (m, 2, OCH$_2$), 2.4–2.2 and 1.95–1.62 (m, 5, 5CH).

Anal. Calcd. for $C_{13}H_{14}N_2O_2Cl_2$·0.02 $C_2H_5OH$: C, 51.85; H, 4.71; N, 9.27; Cl, 23.47. Found: C, 51.87; H, 4.74; N, 9.28; Cl, 23.60.

EXAMPLE 9

(±-(1R*, 2R*, 4S*)-4-(Acetoxmethyl)-2-(5,6-dichloro-1H-benzimidazol-1-yl) cyclopentyl acetate (±)-(1R*, 2R*,4S*)-2-(5,6-Dichloro-1H-benzimidazol-1-yl)-4-(hydroxymethyl) cyclo-pentanol (7.80 g, 25.8 mmol) was dissolved in pyridine (50 mL)-acetic anhydride (50 mL) and the solution stirred overnight. Volatiles were removed in vacuo and the residual oil partitioned between methylene chloride (150 mL) and saturated aqueous sodium bicarbonate (100 mL). The organic layer was dried (sodium sulfate) and evaporated to a glass (9.91 g, 99%); $^1$H-NMR (DMSO-$d_6$) δ: 8.58, 8.08, 7.96 (s, 3, aryl CH), 5.39–5.32 (m, 1, OCH), 5.09–5.04 (m, 1, NCH), 4.11 (d, J=6.6 Hz, 2, $OCH_2$), 2.59–2.50 (m overlapping solvent, CH), 2.41–2.35 (m, 1, CH), 2.17–1.86 (m overlapping 2.06 and 1.94, both s, total 9, 3CH and $2CH_3CO$).

Anal. Calcd. for $C_{17}H_{18}N_2O_2Cl_2 \cdot 0.1\ CH_2Cl_2$: C, 52.96; H, 4.70; N, 7.26; Cl, 18.55. Found: C, 52.86; H, 4.74; N, 7.25; Cl, 18.50.

EXAMPLE 10

(±)-(1R*, 2R,4S*)-4-(Acetoxymethyl)-2-(2-bromo-5,6-dichloro-1H-benzimidazol-1-yl)-cyclopentyl acetate N-Bromosuccmimide (4.54 g, 25.5 mmol) was added to a solution of (±)-(1R*, 2R*,4S*)-4-(acetoxymethyl)-2-(5,6-dichloro-1H-benzimidazol-1-yl) cyclopentyl acetate (8.95 g, 23.2 mmol) in dry N,N-dimethylformamide (46 mL). The solution was maintained at ca. 70° C. (oil bath) for 5 hours. Volatiles were removed in vacuo and the residual orange syrup chromatographed on silica gel. Title compound was eluted with chloroform as a pale yellow solid (5.14 g, 48%), m.p. 122–125° C.; $^1$H-NMR (DMSO-$d_6$)δ: 8.16 (s, 1, benzimidazole H7), 7.95 (s, 1, benzimidazole H4), 5.60–5.55 (m, 1, OCH), 5.12–5.03 (m, 1, NCH), 4.15 (d, J=6.3 Hz, 2, $OCH_2$), 2.66–2.60 (m, 1, $CHCH_2$), 2.29–2.14 (m, 3, CH), 2.06 (s, 3, $CH_3CO$), 1.93 (s overlapped by m, 4, $CH_3\ CO$ +CH); mass spectrum (Cl): 469 (5.8), 467 (37.5), 465 (95), 463 (54, M+1), 199 (100, M-B).

Anal. Calcd. for $C_{17}H_{17}N_2Cl_2BrO_4$: C, 43.99; H, 3.69; N, 6.04; total halogen as Br, 51.65. Found: C, 44.06; H, 3.70; N, 5.97; total halogen as Br, 51.74.

EXAMPLE 11

Analysis of (−)-(1S, 4R)-4-Amino-2-cyclopentene-1-methanol and its enantiomer, (+)-(1R, 4S)-4-amino-2-cyclopentene-1-methanol Samples of the title compounds were characterized by the method of Bückner, H., Wittner, R., and Godel, H., "Automated Enantioseparation of Amino Acids by Derivatization with o-Phthaldialdehyde and N-Acylated Cysteines", J. Chrom., 476 (1989)73–82. Using o-phthaldialdehyde and N-acetyl-L-cysteine as derivatizing reagents. The chromatographic separation used an Optima II ODS 100×4.5 mm, 3 µm column (HI Supplies Co., Meriden, Conn.) and gradient elution at 0.9 mL/min using initially 100% sodium acetate buffer, 40 mM, pH 6.5, with a linear ramp to 18% acetonitrile over 15 minutes and a subsequent hold at 18% acetonitrile for 15 minutes. Detection was at 338 nm. Samples were dissolved in 0.1 molar borate buffer, pH 10.4. The identity and purity of the samples was established by comparison with authentic standards (see EP 434450 (Jun. 26, 1991)). The retention time of the (1S, RS) isomer was about 21 minutes. The retention time of the (1 R, 4S)- isomer was about 22 minutes.

EXAMPLE 12

(±)-cis4-Amino-2-cyclopentene-1-methanol

A dry, 2L, three-neck flask was equipped with a mechanical stirrer, thermometer with gas inlet adapter connected to the nitrogen supply, and septum. The flask was purged with nitrogen, immersed in an ice-acetone bath, and lithium aluminum hydride solution in tetrahydrofuran (1.0 molar, 800 mL, 0.80 mol, Aldrich) was added via cannula. Dry tetrahydrofuran (2×15 µL) was used to rinse in the lithium aluminum hydride solution. When the solution had cooled to 0° C., the slurry of (±)-cis4-amino-2-cyclopentene-1-carboxylic acid 4-toluenesulfonate salt in tetrahydrofuran was cannulated in with good stirring, at such a rate as to keep the temperature less than 10° C. and moderate the hydrogen evolution (about one hour). The flask was rinsed with dry tetrahydrofuran (2×15 mL), and the septum was replaced with a reflux condenser. The resulting clear, light amber solution was slowly warmed to a gentle reflux over the course of two hours, at which point it became cloudy. After refluxing overnight (16 hours), the heating bath was dropped, sodium fluoride (136.3 g, 3.25 mol, reagent grade powder) was added, and the condenser reset for downward distillation. The mixture was distilled to a thin slurry (700 mL of distillate collected), then cooled in an ice bath. Diethyl ether (dry, 500 mL) was added, and the condenser was replaced by an addition funnel containing water (43 mL, 2.4 mol). The water was added very slowly (two hours), with care taken to control the rate of hydrogen evolution and maintain the temperature at 10±5° C. Meanwhile, water (54 mL) was added to the above recovered distillate, and sufficient additional tetrahydrofuran was added to bring the total volume to 900 mL (6% $H_2O$). The reaction mixture was filtered by suction, and the cake displace-washed with tetrahydrofuran (100 mL). Part of the 6% water-tetrahydrofuran solution (300 mL) was used to slurry-wash the cake, which was then returned to the reaction flask. The cake was triturated (25 minutes) in 6% water-tetrahydrofuran (400 mL), filtered, and displace-washed with 6% water-tetrahydrofaran (200 mL). The combined filtrates were concentrated to a pale yellow oil under vacuum (44.07 g, 67.8% by HPLC, see Example 3). This oil, containing pure title compound, water, and a trace of tosylate salt, darkens rapidly under ambient conditions. It was immediately reacted to form the N-BOC derivative, a stable, crystalline solid, (see the following Example). The filter cake was returned to the flask and triturated in methanol (800 mL) for 48 hours. The resulting slurry was filtered under a rubber dam, and the cake was washed with methanol (200 mL). The filtrate was concentrated under vacuum to a yellow solid (56.80 g, 20.9% yield by HPLC; total overall yield 88.7%).

EXAMPLE 13

(±)-cis-4-Amino-2-cyclopentene-1-methanol

By the method of Example 12 but on about twice the scale (97.40 g, 0.8924 mol of (±)-2-azabicyclo[2.2.1]hept-5-en-3-one) the title compound was obtained as extracts containing the title compound (0.7926 mol, 88.8% of theoretical, allowing for aliquots removed, as determined by the method of Example 11).

EXAMPLE 14

(±)-cis-tert-Butyl N-(4-[hydroxymethyl)-2-cyclopenten-1-yl]carbamate

The combined tetrahydrofuran extracts from the preceding Example were concentrated under vacuum to 1031 g, cooled in an ice-water bath, and a mixture of sodium bicarbonate (97.46 g, 1.16 mol) in water (500 mL) was added. This was followed by di-tert-butyl dicarbonate (204.5 g), 0.9501 mol). The mixture was stirred at 5° C. for two days. The methanol extracts from the preceding Example were evaporated to an oily solid (136.64 g), which was added to the mixture. After warming to room temperature, the organic solvents were evaporated under vacuum, and the resulting slurry was extracted with hexanes, three portions of methylene chloride, then hexanes again (200 mL each). The organic extracts were evaporated to an oil, which was crystallized from hexanes (about 300 mL), giving the title compound (154.15 g, 0.7229 mol). Additional product was obtained by chromatography of the mother liquors (10.5 g, 0.0491 mol, 86.6% of theoretical from the starting lactam, allowing for aliquots removed).

EXAMPLE 15

(±)-cis-[4-(4,5-Dichloro-2-nitroanilino)-2-cyclopenten-1-yl]methanol (±)-cis-tert-Butyl N-[4-(hydroxymethyl)-2-cyclopenten-1-yl]carbamate (50.0 g, 0.230 mole) was stirred in 25% trifluoroacetic acid in methylene chloride (1.5 L) at 0° C. for 1.0 hour. Evaporation of volatiles left the trifluroacetic acid salt of the amine described in Example 27 as a dark oil. To this oil were added t-butanol (350 mL), potassium carbonate (65 g), and 1,2,4-trichloro- 5-nitrobenzene (Aldrich, 54.7 g, 0.230 mole as 97%). The resulting mixture was refluxed with vigorous stirring for 3 days. Volatiles were removed under vacuum and the residue triturated with methanol. The methanol-soluble material was chromatographed on silica gel. Crude product was eluted with 2% methanol-chloroform to give orange solid (38.0 g). Crystallization from ethyl acetate-hexanes gave title compound as orange crystals (34.0 g, 49%), m.p. 96–98° C.; $^1$H-NMR(DMSO-$d_6$) and mass spectrum(CI) consistent with structure and identical with samples of chiral enantiomers described in Examples 18 and 26.

Anal. Calcd. for $C_{12}H_{12}N_2C_{12}O_3$: C, 47.55; H, 3.99: N, 9.24 Cl, 23.39. Found: C, 47.75; H, 4. 10; N, 9.20; Cl, 23.52.

Continued elution of the column gave further fractions containing title compound with minor low $R_f$ impurities. These fractions were combined with the mother liquor from the above crystallization and recrystallized from ethyl acetate-hexanes to give additional orange solid (16.7 g) having identical $^1$H-NMR spectrum and bringing the total yield to 73%.

EXAMPLE 16

(±)-(1R*, 2S*, 3S*, 5S*)-3-(Acetoxethyl)-5-(4.5-dichloro-2-nitroanilino)-1,2-cyclopentanediyl diacetate and (L) (1R*, 2S*, 3R*, 5R*)--3-(acetoxymethyl)-5-(4,5-dichloro-2-nitroanilino)-1,2-cyclopentanediyl diacetate To a solution of (±)-cis-[4-(4,5-dichloro-2-nitroanilino)-2-cyclopenten-1-yl]methanol (20.0 g, 66.0 mmol) and N-methylmorpholine N-oxide (Aldrich, 60% aqueous solution, 12.0 mL, 69 mmol) in acetone (280 mL) was added osmium tetroxide (2.5% in t-butyl alcohol, Aldrich, 1.24 mL). After stirring at ambient temperature for 18 hours, volatiles were removed in vacuo and the residue stirred with pyridine (200 mL)-acetic anhydride (40 mL) for an additional 18 hours. The solution was concentrated to a thick red oil which was partitioned between saturated aqueous sodium carbonate and chloroform. The chloroform layer was dried (sodium sulfate) and then concentrated to an oil in vacuo. A mixture of the isomeric title compounds was eluted from a silica gel column with 2% methanol-chloroform and crystallized from ethyl acetate-hexanes (with seeding by crystals of the (1R*,2S*)-isomer prepared by the method of Example 1) to give (±)-(1R*, 2S*, 3S*, 5S*)-3-(acetoxymethyl)-5-(4,5-dichloro-2-nitroanilino)-1,2-cyclopentanediyl diacetate as orange crystals (17.4 g, 57%), m.p. 154–156° C.; $^1$H-NMR(DMSO-$d_6$) identical to that of the sample described in Example 1.

Continued crystallization of the mother liquor contents from ethyl acetate-hexanes gave (±)(1R*, 2S*, 3R*, 5R*)-3-(acetoxymethyl)-5-(4,5-dichloro-2-nitroanilino)-1,2-cyclopentanediyl diacetate as orange crystals (8.82 g, 29%), m.p. 105–107° C.; $^1$H-NMR(DMSO-$d_6$).

Anal. Calcd. for $C_{18}H_2ON_2Cl_2O_8$: C, 46.67; H, 4.35; N, 6.05; Cl, 15.31. Found: C, 46.50; H, 4.33; N, 5.96; Cl, 15.23.

EXAMPLE 17

(±)(1R*, 2S*, 3R*, 5R*)-3-(Acetoxymethyl)-5-(2-bromo-5,6-dichloro-1H-benzimidazol-1-yl)-1,2-cyclopentanediyl diacetate (±)( 1R*, 2S*, 3R*, 5R*)-3-(Acetoxymethyl)-5-(4,5-dichloro-2-nitroanilino)-1,2-cyclopentanediyl diacetate (5.00 g, 10.8 mmol) was stirred in ammonia/methanol (ca. 2 N, 100 mL) at ambient temperature for 18 hours. Evaporation of volatiles in vacuo left residual orange solid (±)-(1R*, 2S*, 3R*, 5R*)-5-(4,5-dichloro-2-nitroanilino)-3-(hydroxymethyl)-1,2-cyclopentanediol having an identical $R_f$ on silica gel TLC plates to that of the chiral sample described in Example 19. This solid was reduced with Raney nickel/hydrogen(45 psi) in isopropanol (200 mL). Catalyst was filtered off with Celite. The filtrate-wash was evaporated to dryness in vacuo. The residue was refluxed in formic acid (96%, 50 mL) for one hour, as described in Example 2. The oil remaining on evaporation of the formic acid was dissolved in methanol. The pH was adjusted to 13 with aqueous 5 N sodium hydroxide and the solution was stirred at ambient temperature for one hour to hydrolyze formate esters. The pH was adjusted to 7 with 1 N hydrochloric acid and volatiles removed by evaporation in vacuo. Pyridine (100 mL) and acetic anhydride (4 mL) were added to the residue and the mixture stirred at ambient temperature overnight. Evaporation of volatiles in vacuo followed by chromatography on silica gel with 1% methanol-chloroform gave (±)(1R*, 2S*, 3R*, 5R*)-3-(acetoxyethyl)-5-(5,6-dichloro-1H-benzmidazol-1-yl)-1,2-cyclopentanediyl diacetate as white crystals from ethanol-water (2.6 g, 53%), $^1$H-NMR(DMSO-$d_6$) consistent with structure. (±)(1R*, 2S*, 3R*, 5R*)-3-(Acetoxymethyl)-5-(5,6-dichloro-1H-benzimidazol-1-yl)-1,2-cyclopentanediyl diacetate (2.5 g, 5.7 mmol) was dissolved in dry dioxane (15 mL) and the solution refluxed while freshly recrystallized N-bromosuccinimide (2.10 g, 11.5 mmol) was added all at once. After 5 minutes of reflux, the red-brown solution was evaporated in vacuo to a red oil. A chloroform solution of this oil was washed with water and then dried (sodium sulfate). The chloroform solution was concentrated to an oil which was chromatographed on silica gel. Product-containing fractions were eluted with 2–4% methanol-chloroform. Crystallization from ethyl acetate-hexanes gave as off-white solid (1.5 g, 50%); $^1$H-NMR(DMSO-$d_6$) consistent with structure of title compound. Such a sample was rechromatographed on silica gel with elution by chloroform to give (±)(1R*, 2S*, 3R*, 5R*)-3-(acetoxymethyl)-5-(2-bromo-5,6-dichloro-1H-benzimidazol-1-yl)-1,2-cyclopentanediyl diacetate as white crystals, after crystallization from ethyl acetate-hexanes, m.p. 166–167° C.; $^1$H-NMR(DMSO-$d_6$) δ: 8.14 and 7.96 (both s, 1 each, 2 aromatic CH), 5.6–5.35 (m, 3, 2 OCH and NCH), 4.4–4.1

(m, 2, OCH$_2$), 2.8–2.4 (m overlapping solvent, 2 CH), 2.4–2.1 (m overlapping s at 2.25, total 4, CH and CH$_3$), 2.04 (s, 3, CH$_3$), 1.37 (s, 1, CH$_3$); mass spectrum(CI): 525(53), 523(100), 521(54, M+1). Anal. Calcd for C$_{19}$H19N$_2$BrCl$_2$O$_6$: C, 43.70; H, 3.67; N, 5.37; total halogen as Cl, 20.37. Found: C, 43.65; H, 3.68; N, 5.35; total halogen as Cl, 20.32.

EXAMPLE 18

(1S, 4R)-[4-(4,5-Dichloro-2-nitroanilino)-2-cyclopenten-1-yl]methanol (−)-(1R, 4S)-tert-Butyl N-[4-hydroxymethyl)-2-cyclopenten-1-yl]carbamate (15.00 g, 70.3 mmol) was converted by the method of Example 1 to (1S, 4R)-[4-(4,5-dichloro-2-nitroanilino)-2-cyclopenten-1-yl]methanol, isolated as a yellow powder after elution from a silica gel column with 1:1 hexanes-chloroform and resolidification from ethyl acetate-hexanes (9.97 g, 47%), m.p. 94.5–96.5° C.; $^1$H-NMR(DMSO-d$_6$) δ: 8.24 (s, 1, benzimidazole CH), 8.09 (d, J=8.1 Hz, 1, NH), 7.51 (s, 1, benzimidazole CH), 5.95 and 5.85 (both m, 2, CH=CH), 4.9–4.7 (m overlapping t at 4.78, J=5.1 Hz, total 2, CHN and OH), 3.4 (m, 2, CH$_2$O), 2.80 (m, 1, CH), 2.6–2.4 (m overlapping solvent, CH), 1.5–1.4 (m, 1, CH); mass spectrum(CI): 303 (M+1); [a]$^{20}$589$^{+199°}$, [a]$^{20}$57$^{8++222°}$, [a]$^{20}$546$^{+333°}$ (c=0.267, methanol).

Anal. Calcd. for C$_{12}$H$_{12}$N$_2$Cl$_2$O$_3$Ω0.18 C$_6$H$_1^4$: C, 49.30; H, 4.59; N, 8.79; Cl, 22.25. Found: C, 49.64; H, 4.64; N, 8.68; Cl, 22.10.

EXAMPLE 19

(1S, 2R, 3R, 5R)-5-(4,5-Dichloro-2-nitroanilino)-3-(hydroxymethyl)-1,2-cyclopentanediol and (1R, 2S, 3R, 5R)-5-(4,5-dichloro-2-nitroanilino)-3-(hydroxymethyl)-1,2-cyclopentanediol To a solution of (1 S, 4R)-[4-(4,5-dichloro-2-nitroanilino)-2-cyclopenten-1-yl]methanol (8.60 g, 27.6 mmol) and N-methylmorpholine N-oxide (Aldrich, 60% aqueous solution, 5.02 mL, 29.0 mmol) in acetone (90 mL) was added osmium tetroxide (Aldrich, 2.5% in t-butyl alcohol, 0.51 mL). After stirring at ambient temperature for 18 hours, an additional 0.25 mL of 60% aqueous N-methylmorpholine N-oxide was added and the solution stirred for an additional 5 hours. Volatiles were evaporated in vacuo and the residue recrystallized twice from 95% ethanol to give (1S, 2R, 3R, 5R)-5-(4,5- dichloro-2-nitroanilino)-3-(hydroxymethyl)-1,2-cyclopentanediol as yellow powder (1.78 g, 19%), m.p. 197–199° C.; $^1$H-NMR (DMSO-d$_6$) δ: 8.23 (s, 1, benzimidazole CH), 8.1 (d, J=7.0 Hz, 1, NH), 7.50 (s, 1, benzimidazole CH), 5.02 (d, J=4.9 Hz, 1, OH), 4.74 (t, J=5.1 Hz, 1, CH$_2$OH), 4.58 (d, J=5.1 Hz, 1, OH), 4.0–3.8 (m, 1, NCH), 3.8–3.7 (m, 2, 2 OCH), 3.5–3.4 (m, 2, CH$_2$O), 2.45–2.25 ( m, 1, CH), 2.1–1.9 (m, 1, CH), 1.4–1.2 (m, 1, CH); mass spectrum(CI): 337 (M+1); [a]$^{20}$ 589-10620, [α]2578–1180, [α]$^{20}$54$^{6-182°}$ (c=0.273, methanol).

Anal. Calcd. for C$_{12}$H$_{14}$N$_2$Cl$_2$O$_5$: C, 42.75; H, 4.19; N, 8.31; Cl, 21.03. Found: C, 42.84; H, 4.21; N, 8.24; Cl, 21.09.

Chromatography of the mother liquor contents on silica gel gave the (1R, 2S)-isomer on elution with 7–8% methanol-chloroform; two resolidifications from 90% ethanol gave (1R, 2S, 3R, 5R)-5-(4,5-dichloro-2-nitroanilino)-3-(hydroxymethyl)-1,2-cyclopentanediol as a yellow powder (1.57 g, 17%), m.p. 179–181° C.; $^1$H-NMR(DMSO-d$_6$) δ: 8.70 (d, J =7.1 Hz, 1, NH), 8.22 and 7.32 (both s, 1 each, 2 benzimidazole CH), 5.28 (d, J=5.6 Hz, 1, OH), 4.77 (d, J=3.9 Hz, 1 OH), 4.45 (t, J=4.9 Hz, 1, CH$_2$O:1, 4.1–3.9 (m, 3, 2 OCH and NCH), 3.6–3.5 and 3.45–3.35 (both m partially overlapping H20, 2, CH$_2$O), 2.45–2.25 (m, 1, CH), 2.1–3.9 (m, 1, CH), 1.35–1.25 (m,l, CH); mass spectrum (CI): 337(M+1); [α]$^{20}$589$^{-15.6°}$, [α]$^{20}$54$^{6-4.00°}$ (c=0.250, methanol).

Anal. Calcd. for C$_{12}$H$_{14}$N$_2$Cl2O$_5$: C, 42.75; H, 4.19; N, 8.31; Cl, 21.03. Found: C, 42.87; H, 4.15; N, 8.30; Cl, 21.14.

Elution with 8–10% methanol-chloroform gave white solid (2.9 g) which $^1$H-NMR showed to be an approximately 1:1 mixture of the two isomers.

Continued elution of the column with 10–20% methanol-chloroform gave fractions containing additional (1S, 2R, 3R, 5R)-5-(4,5- dichloro-2-nitroanilino)-3-(hydroxymethyl)-1, 2-cyclopentanediol which solidified from 90% ethanol to white powder (2.23 g) bringing the total yield of this isomer to 43%.

EXAMPLE 20

(1S, 2R, 3R, 5R)-3-(Acetoxymethyl)-5-(4,5-dichloro-2-nitroanilino)-1,2-cyclopentanediyl diacetate (1S, 4R)-[4-(4,5-Dichloro-2-Nitroanilino)-2-cyclopenten-1-yl]methanol (3.75 g, 11.1 mmol) was acetylated in pyridine-acetic anhydride as in Example 16. The crude product was eluted from a silica gel column with 2% methanol-chloroform and solidified from ethyl acetate to give (1S, 2R, 3R, 5R)-3-(acetoxymethyl)-5-(4,5-dichloro-2-nitroanilino)-1,2-cyclopentanediyl diacetate as yellow powder (5.13 g, 100%), NMR identical to that of Example 1. Such a sample was crystallized from ethyl acetate-hexanes to give title compound as yellow powder, m.p. 128–130° C.; $^1$H-NMR(DMSO-d$_6$) and mass spectrum (CI) identical to those of Example 1.; [α]$^{20}$589 $^{-95.8°}$, [α]$^{20}$57$^{8-107°}$, [α]$^{20546-165°}$ (c=0.259, methanol).

Anal. Calcd. for C$_{18}$H$_2$ON$_2$Cl$_2$O$_8$: C, 46.67; H, 4.35; N, 6.05; Cl, 15.31. Found: C, 46.74; H, 4.36; N, 5.96; Cl, 15.38.

EXAMPLE 21

(1S, 2R, 3R, 5R)-3-(Acetoxymethyl)-5-(5,6-dichloro-1H-benzimidazol-1-yl)-1,2-cyclopentanediyl diacetate (1S, 2R, 3R, 5R)-3-(Acetoxymethyl)-5-(4,5-dichloro-2-nitroanilino)- 1,2-cyclopentanediyl diacetate (4.42 g, 9.97 mmol) was converted to title compound as with the racemic sample described in Example 2. Crude product was chromatographed on silica gel with elution by 5% methanol-chloroform and solvents evaporated to give (1S, 2R, 3R, 5R)-3-(acetoxymethyl)-5-(5,6-dichloro-1H-benzimidazol-1-yl)-1,2-cyclopentanediyl diacetate as an off-white solid foam from ethanol (4.0 g, 90%); $^1$H-NMR(DMSO-d$_6$) and mass spectrum(CI) identical to those of racemate described in Example 2; [α]$^{20}$589$^+$25.5°, [α]$^{20}$578$^{+26.7°}$, [α]$^{20}$54$^{6+30.6°}$ (c=0.255, methanol).

Anal. Calcd. for C$_{19}$H$_2$ON$_2$Cl$_2$O$_6$: C, 51.49; H, 4.55; N, 6.32; Cl, 16.00. Found: C, 51.33; H, 4.58; N, 16.27; Cl, 15.90.

EXAMPLE 22

(1S, 2R, 3R, 5R)-5-(5,6-Dichloro-1H-benzimidazol-1-yl)-3-(hydroxymethyl)-1,2-cyclopentanediol (1S, 2R, 3R, 5R)-3-(Acetoxymethyl)-5-(5,6-dichloro-1H-benzimidazol-1-yl)-1,2-cyclopentanediyl diacetate (0.96 g, 2.17 mmol) and sodium carbonate (0.230 g, 2.17 mmol) were stirred in water (3 mL)-ethanol(15 mL)-methanol(15 mL) at ambient temperature for 24 hours. The pH was adjusted to 7 with acetic acid and the volatiles removed in vacuo. The residual solid was slurried in water (25 mL) and filtered. Resolidification from 2:1 ethanol-methanol gave (1S, 2R, 3R, 5R)-5-(5,6-dichloro-1H-benzimidazol-1-yl)-3-(hydroxymethyl)-1,2-cyclopentanediol as white powder (408 mg, 60%), m.p. 222–225° C.; $^1$H-NMR(DMSO-$d_6$) δ: 8.49, 8.09, and 7.96 (all s, 1 each, 3 benzimidazole CH), 5.04 (d, J=7.0 Hz, 1, OH), 4.87 (t, J=5.1 Hz, 1, $CH_2OH$), 4.8–4.6 (m overlapping d at 4.76, J=4.3 Hz, 2, NCH and OH), 4.25–4.10 (m, 1, OCH), 3.9–3.8 (m, 1, OCH), 3.6–3.45 (m, 2, $CH_2O$), 2.45–2.25 (m, 1, CH), 2.2–2.0 (m, 1, CH), 1.85–1.65 (m, 1, CH); mass spectrum(CI): 317 (M+1); $[\alpha]^{20}589^{-12.2°}$, $[\alpha]^{20}578^{-12.9°}$, $[\alpha]^{20}54^{6-14.1°}$ (c=0.255, methanol).

Anal. Calcd. for $C_{13}H_{14}N_2Cl_2O_3$: C, 49.23; H, 4.45; N, 8.83; Cl, 22.36. Found: C, 49.25; H, 4.47; N, 8.83; Cl, 22.46.

EXAMPLE 23

(1S, 2R, 3R, 5R)-5-(2-Bromo-5.6-dichloro-1H-benzimidazol-1-yl)-3-(hydroxymethyl)-1,2-cyclopentanediol (1S, 2R, 3R, 5R)-3-(Acetoxymethyl)-5-(5,6-dichloro-1H-benzimidazol-1-yl)-1,2-cyclopentanediyl diacetate (2.00 g, 4.51 mmol) was dissolved in dry N,N-dimethylformamide (9 mL) and heated to 90° C. N-bromosuccinimide (1.62 g, 9.02 mmol) was added in four portions over 5 hours. . Volatiles were evaporated in vacuo. The residue was chromatographed on silica gel and product was eluted with 30–50% ethyl acetate-hexanes as a yellow glass (1.00 g, 43%); $^1$H-NMR(DMSO-$d_6$) consistent with structure. This sample was deblocked with sodium carbonate (203 mg, 1.9 mmol) in water (3 mL)-ethanol(15 mL)-methanol (15 mL) at ambient temperature for 5 hours. The pH was adjusted to 7 with acetic acid. The solution was evaporated to dryness in vacuo and the residue was triturated with water to give white powder which was chromatographed. Elution of a silica gel column with 10–12% methanol-chloroform gave (1S, 2R, 3R, 5R)-5-(2-bromo-5,6-dichloro-1H-benzimidazol-1-yl)-3-(hydroxymethyl)-1,2-cyclopentanediol as white powder after solidification from 1:1 ethanol-methanol (410 mg, 54%), m.p. 212–215° C.; $^1$H-NMR(DMSO-$d_6$) and mass spectrum identical with those of racemate described in Example 4; $[\alpha]^{20}589^{-31.2°}$, $[\alpha]^{20}57^{8-32.3°}$, $[\alpha]^{20}54^{6-37.3°}$ (c=0.260, methanol).

Anal. Calcd. for $C_{13}H_{13}N_2BrCl_2O_3$: C, 39.43; H, 3.31; N, 7.07; total halogen as Cl, 26.86. Found: C, 39.62; H, 3.37; N, 7.02; total halogen as Cl, 26.75.

EXAMPLE 24

(1S, 2R, 3R, 5R)-5-[5,6-Dichloro-2-(cyclopropylamino)-1H-benzimidazol-1-yl]-3-(hydroxymethyl)- 1,2-cyclopentanediol (1S, 2R, 3R, 5R)-3-Acetoxymethyl)-5-(2-bromo-5,6-dichloro-1-H-benzimidazol- 1-yl)-1,2-cyclopentanediyl diacetate (500 mg 0.958 mmole) was refluxed in water:ethanol/2:1 (7.5 mL) with cyclopropylamine (0.66 mL, 9.6 mmole) under nitrogen for 18 hours. TLC (silica gel, 10% methanol-chloroform) showed complete conversion to a single spot with lower $R_f$ than starting material. 1 N sodium hydroxide (0.96 mL) was added and volatiles were evaporated. The residue was chromatographed on a silica gel flash column. Title compound was eluted with 10% methanol-chloroform as a colorless glass which solidified from water:ethanol/2:1 (5 mL) to give off-white powder (207 mg, 59%, m.p. 116–118° C. dec.; $^1$H-NMR(DMSO-$d_6$)δ and mass spectrum: identical with those of enantiomer described in Example 74; $[\alpha]^{20}_{589}$ –12.2°, $[\alpha]^{20}_{578}$–12.5°, $[\alpha]^{20}_{546}$–13.5° (c=0.312, methanol).

Anal. Calcd. For $C_{16}H_{19}N_3Cl2O_3$: C, 51.63; H, 5.15: N, 11.29; Cl, 19.05. Found: C, 51.37; H, 5.10; N, 11.16; Cl, 19.25.

EXAMPLE 25

(1R, 4S)4-Amino-2-cyclopentene-1-methanol

A mixture of (−)-(1 S, 4R)-4-amino-2-cyclopentene-1-carboxylic acid (Chiroscience Ltd., Cambridge, England; 40.00 g, 0.315 mole) in dry tetrahydrofuran (300 mL) was stirred in an ice bath while 1 M lithium aluminum hydride in tetrahydrofuran (Aldrich, 485 mL) was added over 1.5 hours. The temperature during this addition was not allowed to exceed 0° C. The mixture was brought to ambient temperature and then to reflux over one hour and maintained at reflux for 2.5 hours. The mixture was allowed to cool to ambient temperature and sodium fluoride (89.6 g) was added and stirring continued for an additional 0.5 hour. The mixture was cooled (ice bath) and water (23 mL) added slowly. Stirring was continued for an additional 0.5 hour. The precipitate was filtered and extracted with 40% methanol-tetrahydrofuran (2×300 mL). The filtrate-wash was concentrated in vacuo to a colorless oil which darkened rapidly in air and light and was used immediately (Example 16). Such a sample was dried at ambient temperature/0.2 mm Hg to a pale yellow oil; $^1$ H-NMR(DMSO-$d_6$) identical to that of the enantiomer described in Example 22, d: 5.67 (m, 2, CH=CH), 3.8–3.7 (m, 1, CHN), 3.32 (d, J=6.0 Hz, overlapped by broad $D_2O$-exchangeable peak centered at 3.18, $CH_2O$, OH, $NH_2$ and $H_2O$ in solvent), 2.68–2.56 (m, 1, H-1), 2.28–2.18 (m, 1, ½ $CH_2$), 1.08–0.98 (m, 1, ½ $CH_2$); mass spectrum(CI): 114(M+1); $[\alpha]^{20}58^{9+55.0°}$, $[\alpha]^{20}578^{+58.3°}$, $[\alpha]^{20}54^{6+67.4°}$, $[\alpha]^{20}43^{6+119°}$ (c=0.242, methanol).

Anal. Calcd. for $C_6H_{11}NO\Omega0.31$ $H_2O$: C, 60.69; H, 9.86; N, 11.80. Found: 61.12; H, 9.79; N, 11.38.

EXAMPLE 26

(1R, 4S)-[4-(4,5-Dichloro-2-nitroanilino)-2-cyclopenten-1-yl]methanol

The filtrate-wash from Example 25 was concentrated and t-butanol (400 mL) was added to the residual oil. This solution was used for the condensation with 1,2,4-trichloro-5-nitrobenzene (Aldrich, 71.3 g, 0.315 mole as 97%) by the method of Example 10. The reaction mixture, after evaporation of volatiles in vacuo, was chromatographed on a silica gel column eluted with 1:1 hexanes-ethyl acetate and ethyl acetate. Rechromatography of the crude product on silica gel was carried out with elution of by 4–6% methanol-chloroform. Combined product-containing fractions yielded 58 grams of reddish solid on evaporation of solvents. This solid was resolidified from ethyl acetate-hexanes to give (1R, 4S)-[4-(4,5-dichloro-2-nitroanilino)-2-cyclopenten-1-yl]methanol as yellow powder (34.5 g, 36% from (−)-(1S, 4R)-4-amino-2-cyclopentene-1-carboxylic acid); m.p. 95–97° C.; $^1$H-NMR(DMSO-$d_6$) and mass spectrum(CI) identical with those of the enantiomer described in Example 18; $[\alpha]^{20}589^{-195°}$, $[\alpha]^{20}578^{-217°}$, $[\alpha]^{20}54^{6<326°}$(c=0.350, methanol).

Anal. Calcd. for $C_{12}H_{12}N_2Cl_2O_3$: C, 47.55; H, 3.99; N, 9.24; Cl, 23.39. Found: C, 47.56; H, 4.01; N, 9.25; Cl, 23.30.

Continued elution of the column (above) gave additional yellow powder (18.0 g, 19%) which $^1$-NMR showed to be additional title compound contaminated by ca. 15% of (1R, 4S)-[4-(2,5-dichloro-4-nitroanilino)-2-cyclopenten-1-yl] methanol.

EXAMPLE 27

(1R, 2S, 3S, 5S)-3-(Acetoxymethyl)-5-(4,5-dichloro-2-nitroanilino)-1,2-cyclopentanediyl diacetate and (1S, 2R, 3S, 5S)-3-(acetoxymethyl)-5-(4,5-dichloro-2-nitroanilino)-1,2-cyclopentanediyl diacetate (1R, 4S)-[4-

(4,5-Dichloro-2-nitroanilino)-2-cyclopenten-1-yl]methanol (17.00 g, 56.1 mmol) was hydroxylated and the mixture of triols was acetylated as in Example 16. The crude red oil isolated after acetylation was chromatographed on silica gel and a mixture of title compounds eluted with 2% methanol-chloroform. Fractional crystallization from ethyl acetate-hexanes gave (1R, 2S, 3S, 5S)-3-(acetoxymethyl)-5-(4,5-dichloro-2-nitroanilino)-1,2-cyclopentanediyl diacetate as yellow needles in two crops (12.78 g, 49%), m.p. 127–128° C.; $^1$H-NMR (DMSO-$d_6$) and mass spectrum (CI) identical to those of the racemic sample described in Example I and the enantiomer described in Example 55; $[\alpha]^{20}589^{+106°}$, $[\alpha]^{20}578^{+119°}$, $[\alpha]^{20}546^{+184°}$ (c=0.275, methanol).

Anal. Calcd. for $C_{18}H_2ON_2Cl_2O_8$: C, 46.67; H, 4.35; N, 6.05; Cl, 15.31. Found: C, 46.74; H, 4.40; N, 6.09; Cl, 15.22.

Continued fractional crystallization of the mother liquor contents from ethyl acetate-hexanes gave (1S, 2R, 3S, 5S)-3-(acetoxymethyl)-5-(4,5-dichloro-2-nitroanilino)-1,2-cyclopentanediyl diacetate as orange crystals (2.45 g, 10%), m.p. 122–124° C.; $^1$H-NMR(DMSO-$d_6$).

Evaporation of combined mother liquors gave an additional 9.50 g (40%) of an approximately 1:1 (by $^1$H-NMR) mixture of the title compounds.

EXAMPLE 28

(1R, 2S, 3S, 5S)-3-(Acetoxymethyl)-5-(5,6-dichloro-1H-benzimidazol-1-yl)-1,2-cyclopentanediyl diacetate (1R, 2S, 3S, 5S)-3-(Acetoxymethyl)-5-(4,5-dichloro-2-nitroanilino)-1,2-cyclopentanediyl diacetate was converted to title compound as in Example 2. The crude product after formic acid treatment was chromatographed on silica gel with elution by 10% ethyl acetate-hexanes. Evaporation of product-containing fractions left (1R, 2S, 3S, 5S)-3-(acetoxymethyl)-5-(5,6-dichoro-1H-benzimidazol-1-yl)-1,2-cyclopentanediyl diacetate as a white solid foam from ethyl acetate (1.85 g, 95%); $^1$H-NMR(DMSO-$d_6$) and mass spectrum(CI) identical to those of racemate described in Example 2 and enantiomer described in Example 56; $[\alpha]^{20}589^{-25.5°}$, $[\alpha]^{20}578^{-27.020}$, $[\alpha]^{20}546^{-31.2°}$ (c=0.333, methanol).

Anal. Calcd. for $C_{19}H_2ON_2Cl_2O_6 \cdot 0.1$ EtOAc: C, 51.54; H, 4.64; N, 6.20; Cl, 15.68. Found: C, 51.29; H, 4.69; N, 6.19; Cl, 15.91.

EXAMPLE 29

(1S, 2R, 3S, 5S)-5-(5,6-Dichloro-1H-benzimidazol-1-yl)-3-(hydroxymethyl)-1,2-cyclopentanediol and (1RK 2S, 3S, 5S)-5-(5,6-Dichloro-1H-benzimidazol-1-yl)-3-(hydroxymethyl)-1,2-cyclopentanediol An ca. 1:1 mixture of (1R, 2S, 3S, 5S)-3-(acetoxymethyl)-5-(4,5-dichloro-2-nitroanilino)-1,2-cyclopentanediyl diacetate and (1S, 2R, 3S, 5S)-3-(acetoxymethyl)-5-(4,5-dichloro-2-nitroanilino)-1,2-cyclopentanediyl diacetate (4.30 g, 9.28 mmol) was deacetylated with sodium carbonate (97 mg) in 1:1:1 water-ethanol-methanol (100 mL) at ambient temperature for 24 hours. The pH was adjusted to 7 with acetic acid and the volatiles removed in vacuo. The residual solid was extracted with methanol. The methanol filtrate was evaporated to dryness in vacuo. The residual solid was dissolved in ethanol (55 mL)-water (20 mL), adjusted to pH 5–6 with sulfuric acid, and refluxed with iron powder (325 mesh, 99.9%, Aldrich, 5.18 g, 93 mequiv) and iron(II) sulfate heptahydrate (Aldrich, 98+%, 1.30 g, 4.58 mequiv) for 4 hours. Solids were filtered off and the ethanol filtrate-wash concentrated to an oil. Triethylorthoformate (55 mL) and methanesulfonic acid (0.05 mL) were added to the oil and the resulting solution stirred at ambient temperature for 18 hours. Concentration in vacuo left an oil which was redissolved in 1 N hydrochloric acid (50 mL)-dioxane(5 mL). After 2.5 hours, the pH was adjusted to 7 with 1 N sodium hydroxide and the volatiles evaporated in vacuo. The residual solids were chromatographed on silica gel. Elution with 10–12% methanol-chloroform gave fractions containing (1S, 2R, 3S, 5S)-5-(5,6-dichloro-1H-benzimidazol-1-yl)-3-(hydroxymethyl)-1,2-cyclopentanediol, which was isolated as white crystals (540 mg, 18%) after crystallization from ethyl acetate-hexanes, m.p. 201–202° C.; $^1$H-NMR (DMSO-$d_6$)d: 8.42, 8.07, and 7.92 (all s, 1 each, 3 benzimidazole CH), 5.1–4.8 (m overlapping d at 5.02, J=5.7 Hz, and d at 4.93, J =3.9 Hz. total 3, NCH and 2 OH), 4.54 (t, J=4.8 Hz, 1, OH), 4.2–4.0 (m, 2, 2 OCH), 3.75–3.45 (m, 2, OCH$_2$), 2.4–1.9 (m, 3, CH$_2$ and CH); mass spectrum(CI): 317 (M+1); $[\alpha]^{20}589^{-61.4°}$, $[\alpha]^{20}578^{-63.1°}$, $[\alpha]^{20}546^{-72.9°}$ (c=0.350, methanol).

Anal. Calcd. for $C_{13}H_{14}N_2Cl_2O_3$: C, 49.23; H, 4.45; N, 8.83; Cl, 22.36. Found: C, 49.20; H, 4.45; N, 8.78; Cl, 22.37.

Continued elution of the column with 15–20% methanol-chloroform gave fractions containing a mixture of the title compounds followed by fractions containing only (1R, 2S, 3S, 5S)-5-(5,6-dichloro-1H-benzimidazol-1-yl)-3-(hydroxymethyl)-1,2-cyclopentanediol, which was isolated as white crystals (605 mg, 21%) on crystallization from 10% methanol-ethyl acetate, m.p. 221–222° C.; $^1$H-NMR (DMSO-$d_6$) and mass spectrum(CI) 317(M+1); $[\alpha]^{20}589^{+14.5°}$, $[\alpha^{20}578^{+15.2°}$, $[\alpha]^{20}546^{+16.9°}$ (c=0.290, methanol).

Anal. Calcd. for $C_{13}H_{14}N_2C_2O_3$: C, 49.23; H, 4.45; N, 8.83; Cl, 22.36. Found: C, 49.29; H, 4.46; N, 8.87; Cl, 22.26.

EXAMPLE 30

(1R, 2S, 3S, 5S)-3-(Acetoxymethyl)-5-(2-bromo-5,6-dichloro-1H-benzimidazol -1-yl)-1,2-cyclopentanediyl diacetate (1R, 2S, 3 S, 5S)-3-(Acetoxymethyl)-5-(5,6-dichloro-1H-benzimidazol-1-yl)-1,2-cyclopentanediyl diacetate (1.40 g, 2.94 mmol) was brominated as in Example 3. Volatiles were removed in vacuo and the residue chromatographed on silica gel. Crude product eluted with 20–30% hexane-ethyl acetate as a colorless oil. A chloroform solution of the oil was washed with water in order to remove contaminating succinimide. The chloroform solution was dried (sodium sulfate) and evaporated to dryness in vacuo to give title compound as white solid foam from ethanol (760 mg, 50%); $^1$H-NMR (DMSO-$d_6$) and mass spectrum(CI) identical to racemate described in Example 3; $[\alpha]^{20}589^{+43.8°}$, $[\alpha]^{20}578+45.2°$, $[\alpha]^{20}546^{52.2°}$ (c=0.345, methanol).

Anal. Calcd. for $C_{19}H_{19}N_2BrCl_2O_6 \cdot 0.05$ EtOH: C, 43.74; H, 3.71; N, 5.34; total halogen as Cl, 20.28. Found: C, 43.74; H, 3.69; N, 5.35; total halogen as Cl, 20.41.

EXAMPLE 31

(1R, 2S, 3S, 5S)-5-(2-Bromo-5,6-dichloro-1H-benzimidazol-1-yl)-3-(hydroxymethyl)-1,2-cyclopentanediol (1R, 2S, 3S, 5S)-3 -(Acetoxymethyl)-5-(5,6-dichloro-1H-benzimidazol-1-yl)-1,2-cyclopentanediyl diacetate (660 mg, 1.26 mmol) was deacetylated as in Example 4 to give title compound as white powder after solidification from 1:1 ethanol-methanol (415 mg, 83%), m.p. 213–216° C.; $^1$H-NMR(DMSO-$d_6$) and mass spectrum(CI) identical with those of racemate described in Example 4; $[\alpha]^{20}589^{+35.9°}$, $[\alpha^{20}578^{+36.8°}$, $[\alpha]^{20}546^{+42.1°}$ (c=0.340, methanol).

Anal. Calcd. for $C_{13}H_{13}N_2BrCl_2O_3$: C, 39.43; H, 3.31; N, 7.07; total halogen as Cl, 26.86. Found: C, 39.48; H, 3.29; N, 7.00; total halogen as Cl, 26.90.

EXAMPLE 32

(1R, 2S, 3S, 5S)-5-[5,6-Dichloro-2-(cyclopropylamino)-1H-benzimidazol-1-yl]-3-(hydroxymethyl)-1,2-cyclopentanediol (1R, 2S, 3S, 5S)-3-(Acetoxymethyl)-5-(2-bromo-5,6-dichloro-1H-benzimidazol-1-yl)-1,2-cyclopentanediyl diacetate (500 mg, 0.958 mmole) was refluxed in water: ethanol/2:1 (7.5 mL) with cyclopropylamine (freshly opened ampoule from Aldrich, 0.66 mL, 9.6 mmole) under nitrogen for 18 hours. TLC (silica gel, 10% methanol-chloroform) showed complete conversion to a single spot with lower $R_f$ than starting material. 1 N sodium hydroxide (0.96 mL) was added and volatiles were evaporated. The residue was chromatographed on a silica gel flash column. Title compound was eluted with 10% methanol-chloroform as a colorless glass which solidified from water:ethanol/2:1 (5 mL) to give white powder (170 mg, 48%), m.p. 219–220° C.; $^1$H-NMR (DMSO-$d_6$)δ: 7.64 and 7.46 (both s, 2, aromatic CH), 7.1 1 (m, 1, NH), 5.11 (t, J=4.3 Hz, 1, OH), 4.77 (d, J=7.0 Hz, 1, OH), 4.67 (d, J=3.7 Hz, 1, OH), 4.65–4.30 (m, 2, OCH and NCH), 3.85–3.75 (m, 1, OCH), 3.7–3.4 (m, 2, OCH$_2$), 2.85–2.70 (m, 1, NCH of cyclopropyl), 2.15–1.80 (m, 3, CH$_2$ and CH of cyclopentane), 0.80–0.50 (m, 4, 2 CH$_2$ of cyclopropyl); mass spectrum (CI): 372(M+1); $[α]^{20}58^{9+13.4°}$, $[α]^{20}578^{+15.5°}$, $[α]^{20}54^{6+16.9°}$ (c=0.277, methanol). [See Examples 26–28 and 30]

Anal. Calcd. for $C_{16}H_{19}N_3Cl_2O_3$: C, 51.63; H, 5.15: N, 11.29; Cl, 19.05. Found: C, 51.36; H, 5.06; N, 11.25; Cl, 19.16

EXAMPLE 33

(1R, 2S, 3S, 5S)-5-[5,6-Dichloro-2-(isopropylamino)-1H-benzimidazol-1-yl]-3-(hydroxymethyl)-1,2-cyclopentanediol (1R, 2S, 3S, 5S)-3-(Acetoxymethyl)-5-(2-bromo-5,6-dichloro-1H-benzimidazol-1-yl)-1,2-cyclopentanediyl diacetate (1.00 g, 1.92 mmole) was refluxed in ethanol (10 mL) with isopropylamine (1.6 mL, Fluka) under nitrogen for 24 hours. A second portion of isopropylamine (0.80 mL) was added and reflux continued for an additional 4 hours. Volatiles were evaporated, the residue was redissolved in ethanol, 1 N sodium hydroxide (1.90 mL) was added, and volatiles were reevaporated. The residue was chromatographed on a silica gel column. Title compound was eluted with 10% methanol-ethyl acetate as a colorless glass. Concentration of an ethanol solution gave title compound as a off-white solid foam (360 mg, 46%). Such a sample was solidified by trituration with 95% water-5% methanol to give title compound as white powder (96%), m.p. 137–138° C.; $^1$H-NMR(DMSO-$d_6$)δ 7.60 and 7.39 (both s, 2, aromatic CH), 6.64 (d, J=7.4 Hz, 1, NH), 5.14 (t, J=4.3 Hz, 1, OH), 4.81 (d, J=7.3 Hz, 1, OH), 4.70 (d, J=3.5 Hz, 1, OH), 4.70–4.50 (m, 1, NCH), 4.50–4.30 (m, 1, OCH), 4.10–4.00 (m, 1, NCH of cyclopropylamino), 3.9–3.75 (m, 1, OCH), 3.70–3.50 (m, 2, OCH$_2$), 2.20–1.80 (m, 3, CH$_2$ and CH of cyclopentane), 1.24 (d, J=6.6 Hz, 6, 2 CH$_3$); mass spectrum (CI): 374(M+1); $[α^{20}58^{9-3.72°}$, $[α]^{20}57^{8-2.60°}$, $[α]^{20}546^{-2.23°}$, $[α]^{20}43^{6-9.67°}$, $[α]^{20}36^{5-51.7°}$ (c=0.269, methanol). [See Examples 16–18 and 20]

Anal. Calcd. for $C_{16}H_{21}N_3Cl_2O_3Ω1.3 H_2O$: C, 48.32; H, 5.98; N, 10.57; Cl, 17.83. Found: C, 48.08; H, 5.91; N, 10.41; Cl. 18.13.

EXAMPLE 34

(±)-(1 R*, 2S*, 3S*, 5S*)-5-(5,6-Dichloro-2-amino-1H-benzimidazol-1-yl)-3-(hydroxymethyl)-1,2-cyclopentanediol (±)(1R*, 2S*, 3S*, 5S*)-3-(Acetoxymethyl)-5-(2-bromo-5,6-dichloro-1H-benzimidazol-1-yl)-1,2-cyclopentanediyl diacetate (750 mg, 1.44 mmol) was dissolved in ethanol (10 mL). Hydrazine hydrate (55%, 0.41 mL, 7.2 mmol) was added and the solution was refluxed for 2 hours. Volatiles were evaporated and the residual white solid was resolidified from ethanol-water and stirred with Raney nickel (preequilibrated under hydrogen) in methoxyethanol (20 mL) for 30 minutes. Catalyst was filtered off and the filtrate made slightly basic with aqueous sodium hydroxide to complete removal of the acetate groups. The solution was neutralized, and volatiles evaporated. The residual solid was recrystallized from ethanol-water to give title compound as pale pink solid (97 mg, 20%), m.p. 283–284° C. dec.; $^1$H-NMR(DMSO-$d_6$)d: 7.61 and 7.30 (both s, 2, aromatic CH), 6.65 (br s, 2, NH2), 5.07 (t, J=4.3 Hz, 1, OH), 4.80 (d, J=7.0 Hz, 1, OH), 4.66 (d, J=3.7 Hz, 1, OH), 4.65–4.50 (m, 1, NCH), 4.45–4.30 (m, 1, OCH), 3.90–4.80 (m, 1, OCH), 3.70–3.40 (two m, 2, OCH$_2$), 2.20–1.80 (m, 3, CH$_2$ and CH of cyclopentane); mass spectrum (CI): 332 (M+1). [See Examples 1–3]

Anal. Calcd. for $C_{13}H_{15}N_3Cl_2O_3$: C, 47.01; H, 4.55; N, 12.65; Cl, 21.35. Found: C, 46.72; H, 4.60; N, 12.46; Cl, 21.08.

EXAMPLE 35

(±)-(1R*, 2R*, 4S*)-2-2-Cyclopropylamino-5,6-dichloro-1H-benzimidazol-1-yl)-4-(hydroxymethyl)cyclopentanol (±)-(1R*, 2R*, 4S*)-4-(Acetoxymethyl)-2-(2-bromo-5,6-dichloro-1H-benzimidazol-1-yl)-cyclopentyl acetate (500 mg, 1.50 mmol) was reacted with cyclopropylamine (0.73 mL) in the manner of Example 32. Crude product was chromatographed on silica gel and title compound eluted with 5% methanol-ethyl acetate as a colorless glass which solidified from ethyl acetate-hexanes to white powder (180 mg, 48%), m.p. 251–253° C.; $^1$H-NMR(DMSO-$d_6$)6: 7.54 and 7.45 (both s, 2, aromatic CH), 5.04 (d, J=5.1 Hz, 1, OH), 4.97 (t, J=4.7 Hz, 1, OH), 4.60–4.50 and 4.50–4.30 (both m, 1 each, NCH and OCH), 3.50 (m, 2, OCH$_2$), 2.80 (m, 1, CH), 2.35–2.10 (m, 1, CH), 2.05–1.80 (m, 3, CH$_2$ and CH of cyclopentane), 1.80–1.60 (m, 1, CH), 0.80–0.50 (1 m, 4, 2CH$_2$ of cyclopropyl); mass spectrum (CI): 356 (M+1). [See Examples 5–7]

Anal. Calcd. for $C_{16}H_{19}N_3Cl_2O_2$: C, 53.97; H, 5.34; N, 11.80; Cl, 19.91. Found: C, 53.72; H, 5.42; N, 11.52; Cl, 19.64.

EXAMPLE 36

(±)-(1R*, 2S*, 3S*, 5S*)-5-[5,6-Dichloro-2-(cyclobutylamino)-1H-benzimidazol-1-yl]-3-(hydroxymethyl)-1,2-cyclopentanediol (±)(1R*, 2S*, 3S*, 5S*)-3-(Acetoxymethyl)-5-(2-bromo-5,6-dichloro-1H-benzimidazol-1-yl)-1,2-cyclopentanediyl diacetate (500 mg, 0.958 mmol) was dissolved in absolute ethanol (7 mL) and cyclobutylamine (0.41 mL, 4.8 mmol) was added. The solution was refluxed under nitrogen for 18 hours. Volatiles were evaporated and the residue stirred in methanol half-saturated with ammonia at 0° C. (20 mL) for 18 hours. Volatiles were removed in vacuo and the residue crystallized from ethanol-water to give title compound as white solid, m.p. 250° C. dec.; $^1$H-NMR(DMSO-$d_6$)δ 7.61 and 7.38 (both s, 1 each, aromatic CH), 7.07 (d, J=7.4 Hz, 1, NH), 5.15 (t, J=3.9 Hz, 1, OH), 4.81 (d, J=7.3 Hz, 1, OH), 4.71–4.45 (m overlapping d at 4.71, J=3.5 Hz, total 2, OH and NCH), 4.40–4.30 (m, 2. OCH and NCH), 3.82–3.80 (m, 1, OCH), 3.72–3.42 (both m, 1 each, OCH$_2$), 2.32–1.67 (three m, 9, 4CH$_2$ and CH); mass spectrum (CI): 386(M+1). [See Examples 5–7]

Anal. Calcd. for $C_{17}H_{21}N_3Cl_2O_3•0.15$ $H_2O•0.05$ $C_2H_5OH$: C, 52.49; H, 5.56; N, 10.74; Cl, 18.12. Found: C, 52.34; H, 5.47; N, 10.52; Cl, 17.99.

EXAMPLE 37

(±)-(1R*, 2S*, 3S*, 5S*)-5-[5,6-Dichloro-2-(1-azetidinyl)-1H-benzimidazol-1-yl]-3-(hydroxymethyl)-1,2-cyclopentanediol (±)(1R*, 2S*, 3S*, 5S*)-3-(Acetoxymethyl)-5-(2-bromo-5,6-dichloro-1H-benzimidazol-1-yl)-1,2-cyclopentanediyl diacetate (500 mg, 0.958 mmol) was dissolved in ethanol (7 mL). Azetidine (Aldrich, 250 mg, 4.4 mmol as 98%) was added and the solution was refluxed under nitrogen for 48 hours. Methanolic ammonia (saturated at 0° C., 20 mL) was added to the cooled solution and this solution was stirred for an additional 18 hours. Volatiles were evaporated, the residue was redissolved in ethanol (10 mL) and 1N sodium hydroxide (0.96 mL) was added. Volatiles were evaporated and the residual solids were triturated with water (3 mL) and filtered. Resolidification of the solid from acetonitrile-methanol gave title compound as white powder (146 mg, 41%), m.p. 221–222° C.; $^1$H-NMR(DMSO-$d_6$)δ 7.78 and 7.53 (both s, 1 each, 2 aromatic CH), 5.05 (t, J=4.3 Hz, 1, OH), 4.91 (d, J=5.3 Hz, 1, OH), 4.59 (d, J =3.7 Hz, 1, OH), 4.45–4.40 (m, 2, OCH and NCH), 4.25–4.15 (m, 4,2 $CH_2N$), 3.82–3.79 (m, 1, OCH), 3.66–3.43 (both m, 1 each, $OCH_2$), 2.40–2.32 (m, 2, $CH_2$), 2.03–1.95 (m, 3, $CH_2$ and NCH); mass spectrum (CI): 372(M+1). [See Examples 8–10]

Anal. Calcd. for $C_{16}H_{19}N_3Cl_2O_3$: C, 51.63; H, 5.14; N, 11.29; Cl, 19.05. Found: C, 51.45; H, 5.10; N, 11.27; Cl, 18.96.

EXAMPLE 38

(±)-(1R*, 2S*, 3R*, 5R*)-5-[5,6-Dichloro-2-(cyclopropylamino)-1H-benzimidazol- 1-yl]-3-(hydroxymethyl)-1,2-cyclopentanediol (±)(1R*, 2S*, 3R*, 5R*)-3-(Acetoxymethyl)-5-(2-bromo-5,6-dichloro-1H-benzimidazol-1-yl)-1,2-cyclopentanediyl diacetate (Example 39, 1.00 g, 1.87 mmol), cyclopropylamine (Aldrich, 1.7 mL, 24 mmol) and absolute ethanol (10 mL) were refluxed under nitrogen for 48 hours. The reaction was cooled and 1 N sodium hydroxide (1.2 mL) was added. Volatiles were evaporated in vacuo and the residual oily solid was chromatographed on silica gel. Elution with 5% methanol—ethyl acetate gave fractions containing white powder (200 mg). Recrystallization from 1:1 water-ethanol gave (±)-(1R*, 2S*, 3R*, 5R*)-5-[5,6-dichloro-2-(cyclopropylamino)-1H-benzimidazol-1-yl]-3-(hydroxymethyl)-1,2-cyclopentanediol as white crystals (180 mg, 40%); m.p. >250° C.; $^1$H-NMR(DMSO-$d_6$)δ 7.70 (m, 1, NH), 7.62 and 7.39 (both s, 1 each, 2 benzimidazole CH), 5.77 (br s, 1, OH), 5.13 (d, J=5.3 Hz, 1, OH), 4.95–4.80 (m, 1, CHN), 4.48 (t, J=4.7 Hz, 1, $CH_2OH$), 4.2–4.0 (m, 2, 2 OCH), 3.7–4.0 (m, 2, $OCH_2$), 2.9–2.65 (m, 1, OCH), 2.2–1.8 (m, 3, $CH_2$ and CH); mass spectrum (CI): 372(M+1). [See Examples 10–14]

Anal. Calcd. for $C_{16}H_{19}N_3Cl_2O_3$: C, 51.63; H, 5.14; N, 11.29; Cl, 19.05. Found: C, 51.53; H, 5.18; N, 11.22; Cl, 18.97.

EXAMPLE 39

(±)-(1R*, 2S*, 3R*, 5S*)-5-[5,6-Dichloro-2-(cyclopropylamino)-1H-benzimidazol-1-yl]-3-methyl-1,2-cyclopentanediol Part A.(±)-(1S*, 2R*, 3R*, 5R*)-5-(5,6-Dichloro-1H-benzimidazol-1-yl)-3-(hydroxymethyl)-1,2-cyclopentanediol (±)-(1R*, 2S*, 3S*, 5S*)-3-(Acetoxymethyl)-5-(5,6-dichloro-1H-benzimidazol-1-yl)-1,2-cyclopentanediyl diacetate (Example 2, 3.00 g, 6.77 mmol) was dissolved in methanol (100 mL). Methanol saturated with ammonia at 0° C. (100 mL) was added and the solution stirred at ambient temperature overnight. Volatiles were evaporated in vacuo and the residual solid slurried with water and filtered to give title compound as tan powder (2.02 g, 94%).

Part B. (±)-(1R*, 2S*, 3R*, 5S*)-5-(5,6-Dichloro-1H-benzimidazol-1-yl)-3-iodo-1,2-cyclopentanediol (±)-(1S*, 2R*, 3R*, 5R*)-5-(5,6-Dichloro-1H-benzimidazol-1-yl)-3-(hydroxymethyl)-1,2-cyclopentanediol (Part A, 2.00 g, 6.31 mmol) was dissolved in dry DMF (15 mL) under nitrogen and cooled (ice bath) while a solution of methyltriphenoxyphosphonium iodide (Aldrich, 3.27 g, 6.94 mmol) in dry DMF (15 mL) was added dropwise over 20 minutes. Stirring was continued in the ice bath for an additional 30 minutes and then at ambient temperature for 18 hours. Volatiles were evaporated in vacuo and the residue chromatographed on silica gel. Product was eluted with 2% methanol-chloroform to give, after evaporation of solvents, a pale yellow powder (750 mg, 28%); $^1$H-NMR(DMSO-$d_6$δ 8.51, 8.08, and 7.97 (all s, 1 each, 3 benzimidazole CH), 5.20 (d, J=6.7 Hz, 1, OH), 5.04 (d, J=4.9 Hz, 1, OH), 4.8–4.6 (m, 1, NCH), 4.3–4.2 (m, 1, OCH), 3.8–3.7 (m, 1, OCH), 3.6–3.4 (m, 2, $CH_2I$), 2.55–2.40 (m, CH overlapping solvent), 2.35–2.20 (m, 1, CH), 1.75–1.50 (m, 1, CH).

Part C. (±)-(1R*, 2S*, 3R*, 5S*)-5-(5,6-Dichloro-1H-benzimidazol-1-yl)-3-methyl-1,2-cyclopentanediyl diacetate (±)-(1R*, 2S*, 3R*, 5S*)-5-(5,6-Dichloro-1H-benzimidazol-1-yl)-3-iodo-1,2-cyclopentanediol (Part B, 0.73 g, 1.71 mmol) in ethanol (200 mL) was shaken with 5% Pd on carbon (140 mg) with triethylamine (0.24 mL) under hydrogen (50 psi) on a Parr shaker for 7.5 hours. The catalyst was filtered off (Celite) and the ethanol filtrate evaporated to a white solid. To this solid was added pyridine (15 mL) and acetic anhydride (1.3 mL). The resulting solution was stirred at ambient temperature for 18 hours. The volatiles were evaporated and the residual oil was dissolved in chloroform (50 mL). The chloroform solution was extracted with aqueous sodium bicarbonate and dried (sodium sulfate). Evaporation of the chloroform left title compound as a yellow glass (560 mg, 85%); $^1$H-NMR(DMSO-$d_6$) δ: 8.61, 8.15, and 7.97 (all s, 1 each, 3 benzimidazole CH), 5.60–5.45 (m, 1, OCH), 5.20–4.95 (m, 2, OCH and NCH), 2.50–2.15 (m, 3, $CH_2$ and CH), 2.09 and 1.95 (both s, 3 each, 2 OAc), 1.20 (d, J =6.5 Hz, 3, $CHCH_3$).

Part D. (±)-(1R*, 2S*, 3R*, 5S*)-5-(2-Bromo-5,6-dichloro-1H-benzimidazol-1-yl)-3-methyl-1,2-cyclopentanediyl diacetate (±)-(1R*, 2S*, 3R*, 5S*)-5-(5,6-Dichloro-1H-benzimidazol-1-yl)-3-methyl-1,2-cyclopentanediyl diacetate (Part C, 550 mg, 1.43 mmol) was dissolved in dry tetrahydrofuran (15 mL). N-bromosuccinimide (520 mg, 2.92 mmol) was added and the resulting solution refluxed vigorously for 10 minutes. An additional portion of N-bromosuccinimide (100 mg) was added and reflux continued an additional 5 minutes. At this point, TLC (silical gel plates developed with 5% methanol-chloroform) showed starting material has been converted to a slightly higher $R_f$ UV-absorbing spot. The reaction mixture was quenched by cooling (ice bath) and diluted with chloroform (50 mL). This solution was washed with water and dried (sodium sulfate). Evaporation left a yellow solid which was chromatographed on silica gel. Title compound was eluted with 5% methanol-chloroform and triturated in ethyl acetate to give white powder (460 mg, 68%), m.p. 235–236° C. dec.; $^1$H-NMR (DMSO-$d_6$) δ: 8.38 and 7.97 (both s, 1 each, 2 benzimidazole CH), 5.75–5.65 (m, 1, OCH), 5.2–5.0 (m, 2, OCH and NCH), 2.11 (s) overlapped by 2.2–2.05 (m, total 6, OAc with $CH_2$ and CH), 1.95 (s, 3, OAc), 1.22 (d, J=6.3 Hz, 3, $CHCH_3$); mass spectrum (CI): 463 (M+1).

Part E (±)-(1R*, 2S*, 3R*, 5S*)-5-[5,6-Dichloro-2-(cyclopropylamino)-1H-benzimidazol- -yl]-3-methyl-1 2-cyclopentanediol (±)-(1R*, 2S*, 3R*, 5S*)-5-(2-Bromo-5,6-dichloro-1H-benzimidazol-1-yl)-3-methyl-1,2-cyclopentanediyl diacetate (Part D, 350 mg, 0.75 mmole) and cyclopropylamine (Aldrich, 0.53 mL) were refluxed in methoxyethanol (5 mL) for 5 hours. 1 N sodium hydroxide (0.75 mL) was added to the cooled reaction mixture and volatiles were evaporated in vacuo. The residue was chromatographed on silica gel. Product was eluted with 5% methanol-chloroform. Recrystallization from methanol-ethyl acetate gave (±)-(1R*, 2S*, 3R*, 5S*)-5-[5,6-dichloro-2-(cyclopropylamino)-1H-benzimidazol-1-yl]-3-methyl-1,2-cyclopentanediol as white crystals (170 mg, 64%); m.p. 231–233 ° C.; $^1$H-NMR (DMSO-$d_6$)δ: 7.48 and 7.39 (both s, 1 each, 2 benzimidazole CH), 7.10 (m, 1, NH), 4.83 (d, J=5.9 Hz, 1, OH), 4.74 (d, J=5.1 Hz, 1, OH), 4.5–4.3 (m, 2, NCH and OCH), 3.7–3.6 (m, 1, OCH), 2.85–2.7 (m, 1, Ce), 2.1–1.8 (m, 2, $CH_2$ and CH), 1.7–1.5 (m, 1, CH), 1.16 (d, J=5.4 Hz, 3, $CHCH_3$), 0.8–0.5 (m, 4, 2 $CH_2$ of cyclopropyl); mass spectrum (CI): 356 (M+1). [See Examples 1 and 2]

Anal. Calcd. for $C_{16}H_{19}N_3Cl_2O_2$: C, 53.95; H, 5.38; N, 11.80; Cl, 19.90. Found: C, 53.75; H, 5.45; N, 11.71; Cl, 19.98.

EXAMPLE 40

(1R, 2S, 3S, 5S)-5-[2-(tert-Butylamino)-5,6-dichloro-1H-benzimidazol-1-yl]-3-(hydroxymethyl)-1,2-cyclopentanediol A solution of (1R, 2S, 3S, 5S)-5-(2-bromo-5,6-dichloro-1H-benzimidazol-1-yl)-3-(hydroxymethyl)-1,2-cyclopentanediol (500 mg, 1.26 mmole) was stirred in tert-butylamine (Aldrich, 98%, 20 mL) in a Parr bomb maintained at 148 ° C. (oil bath) for 48 hours. The bomb was cooled and the resulting pale yellow solution diluted with ethanol containing 1 N sodium hydroxide (1.2 mL). Volatiles were evaporated in vacuo and the residue was chromatographed on silica gel. Title compound was eluted with 10% methanol-chloroform as a colorless oil. The oil was dissolved in absolute ethanol, concentrated to an oil, and triturated with water (3 mL) to give (1R, 2S, 3S, 5S)-5-[2-(tert-butylamino)-5,6-dichloro-1H-benzimidazol-1-yl]-3-(hydroxymethyl)-1,2-cyclopentanediol as white powder (303 mg, 61%), m.p.: collapses to glass at 116–150° C.; $^1$H-NMR(DMSO-$d_6$) δ: 7.63 and 7.43 (both s, 2, aromatic CH), 6.15 (s, 1, NH), 5.08 (t, J=4.3 Hz, 1, OH), 4.85 (d,J=7.4 Hz, 1, OH), 4.71 (d, J=3.8 Hz, 1, OH), 4.7–4.5 (m, 1, NCH), 4.45–4.3 (m, 1, OCH), 3.80 (m, 1, OCH), 3.7–3.4 (m, 2, $OCH_2$), 2.2–1.85 (m, 3, $CH_2$ and CH of cyclopentane), 1.47 (s, 9, 3 $CH_3$); mass spectrum (CI): 388(M+1); $[α]^{20}58^{9-4.0°}$, $[α]^{20}57^{8-4.3°}$, $[α]^{20}546^{-6.0°}$, $[α\ ^{20}43^{6-22.6°}$, $[α]^{20}36^{5-82.1°}$ (c=0.420, methanol). [See Examples 25–28, 30 and 31]

Anal. Calcd. for $C_{17}H_{23}N_3Cl_2O_3$Ω0.40 $H_2O$: C, 51.63; H, 6.07; N, 10.62; Cl, 17.93. Found: C, 51.50; H, 5.99; N, 10.54; Cl, 17.96.

EXAMPLE 41

(±)-(1R*, 2S*, 3S*, 5S*)-5-[2-(tert-Butylamino)-5,6-dichloro-1H-benzimidazol-1-yl]-3-(hydroxymethyl)-1,2-cyclopentanediol A solution of (±)-(1R*, 2S*, 3S*, 5S*)-5-(2-bromo-5,6-dichloro-1H-benzimidazol-1-yl)-3-(hydroxymethyl)-1,2-cyclopentanediol (750 mg, 1.44 mmole) was stirred in tert-butylamine (Aldrich, 98%, 25 mL) in a Parr bomb maintained at 90° C. (oil bath) for 6 days. Volatiles were evaporated in vacuo and the residual solids refluxed in ethanol (30 mL) with aqueous dimethylamine (Aldrich, 40%, 2 mL) for one hour. Volatiles were evaporated and the residual solids chromatographed on silica gel. Elution with 10% methanol-ethyl acetate gave title compound as colorless glass. Solidification from water gave (±)-(1R*, 2S*, 3S*, 5S*)-5-[2-(tert-butylamino)-5,6-dichloro-1H-benzimidazol-1-yl]-3-(hydroxymethyl)-1,2-cyclopentanediol as a white powder (150 mg, 26%); m.p. 130–132° C.; $^1$H-NMR(DMSO-$d_6$) identical with that of the enatiomer described in Example 30. [See Examples 14]

Anal. Calcd. for $C_{17}H_{23}N_3Cl_2O_3$Ω0.65 $H_2O$Ω0.07 $C_2H_5OH$: C, 51.18: H, 5.94; N, 10.47; Cl, 17.63. Found: C, 51.34; H, 6.06; N, 10.37; Cl, 17.58.

EXAMPLE 42

(±)-(1R*, 2S*, 3S*, 5S*)-5-[5,6-Dichloro-2-(isopropylamino)-1H-benzimidazol-1-yl]-3-(hydroxymethyl)-1,2-cyclopentanediol (±)-(1R*, 2S*, 3S*, 5S*)-3-(Acetoxymethyl)-5-(2-bromo-5,6-dichloro-1H-benzimidazol-1-yl)-1,2-cyclopentanediyl diacetate (750 mg, 1.44 mmole) was refluxed in ethanol (10 mL) with isopropylamine (1.22 mL, Aldrich) under nitrogen for 18 hours. A second portion of isopropylamine (1.22 mL) was added and reflux continued for an additional 24 hours. Volatiles were evaporated, the residue was redissolved in ethanol, 1 N sodium hydroxide (1.44 mL) was added, and volatiles were reevaporated. The residue was chromatographed on a silica gel column. Title compound was eluted with 10% methanol-chloroform as a colorless glass. The glass was crystallized from ethyl acetate—hexanes to give (±)-(1R*, 2S*, 3S*, 5S*)-5-[5,6-dichloro-2-(isopropylamino)-1H-benzimidazol-1-yl]-3-(hydroxymethyl)-1,2-cyclopentanediol as white crystals (305 mg, 57%); m.p. 213–214° C.; $^1$H-NMR(DMSO-$d_6$) identical with that of the enantiomer described in Example 23 .[See Examples 1–4]

Anal. Calcd. for $C_{16}H_{21}N_3Cl_2O_3$: C, 51.35; H, 5.66; N, 11.23; Cl, 18.95. Found: C, 51.27; H, 5.69; N, 11.17; Cl, 18.88.

We claim:

1. A compound of formula (I) or (I-1):

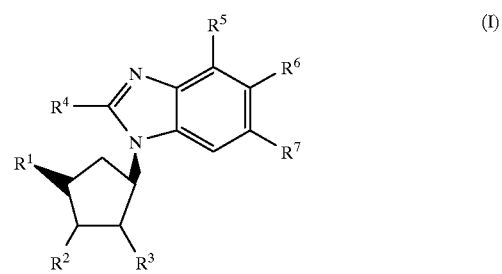

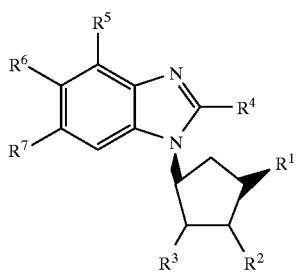

(I-1)

wherein
$R^1$ is H, $CH_3$ or $CH_2OH$; $R^2$ is H or OH; $R^3$ is H or OH; or $R^2$ and $R^3$ together form a bond; $R^4$ is amino, cyclopropylamino, cyclobutylamino, isopropylamino, tert-butylamino or —$NR^8R^9$ where $R^8$ and $R^9$ together with the nitrogen atom to which they are attached form a 4, 5 or 6-membered heterocyclic ring; $R^5$ is H; and $R^6$ and $R^7$ are Cl, excluding the compound (±)-(1R*, 2S*, 3 S*, 5S*)-5-[5,6-Dichloro-2-(cyclopropylamino)-1H-benzimidazol-1-yl]-3-(hyroxyomethyl)-1,2-cyclopentanediol provided that at least one of $R^1$, $R^2$ and $R^3$ is or contains OH; and
pharmaceutically acceptable derivatives thereof.

2. A compound as claimed in claim 1 in which $R^2$ is OH.

3. A compound according to claim 2 wherein $R^4$ is cyclopropylamino, isopropylamino or tert-butylamino.

4. A compound according to claim 3 wherein $R^4$ is isopropylamino or tert-butylamino.

5. A compound according to claim 1 of Formula (IA) or (IA-1)

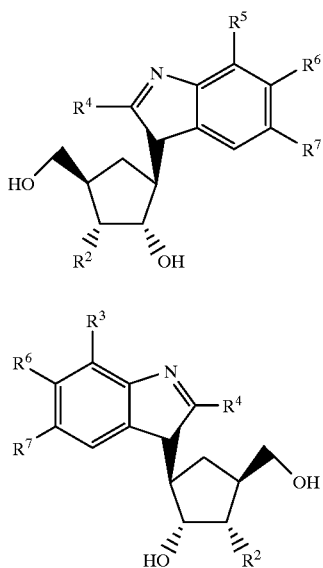

wherein
$R^2$ is H or OH; $R^4$ is amino, cyclopropylamino, isopropylamino, tert-butylamino, or
—$NR^8R^9$ where $R^8$ and $R^9$ together with the nitrogen-atom to which they are attached form a 4, 5 or 6 membered heterocyclic ring; $R^5$ is H; and $R^6$ and $R^7$ are Cl, excluding excluding the compound (±)-(1R*, 2S*, 3S*, 5S*)-5-[5,6-Dichloro-2-(cyclopropylamino)-1H-benzimidazol-1-yl]-3-(hyroxyomethyl)-1,2-cyclopentanediol and pharmaceutically acceptable derivatives thereof.

6. A compound of claim 5 wherein $R^4$ is cyclopropylamino, isopropylamino or tert-butylamino; $R^5$ is H; and $R^6$ and $R^7$ are both Cl; and the pharmaceutically acceptable derivatives thereof.

7. A compound of claim 6 wherein $R^4$ is isopropylamino or tert-butylamino.

8. A compound according to claim 1 which is selected from
(1 R, 2S, 3S, 5S)-5-[5,6-Dichloro-2-(cyclopropylamino)-1H-benzimidazol-1-yl]-3-(hydroxymethyl)-1,2-cyclopentanediol
(1R, 2S, 3S, 5S)-5-[5,6-Dichloro-2-(isopropylamino)-1H-benzimidazol-1-yl]-3-(hydroxymethyl)-1,2-cyclopentanediol
(±)-(1R*, 2S*, 3S*, 5S*)-5-(5,6-Dichloro-2-amino-1H-benzimidazol-1-yl)-3-(hydroxymethyl)-1,2-cyclopentanediol
(±)-(1R*, 2R*, 4S*)-2-(2-Cyclopropylamino-5,6-dichloro-1H-benzimidazol-1-yl)- 4-(hydroxymethyl)cyclopentanol
(±)-(1R*, 2S*, 3S*, 5S*)-5-[5,6-Dichloro-2-(cyclobutylamino)-1H-benzimidazol-1-yl]-3-(hydroxymethyl)-1,2-cyclopentanediol
(±)-(1R*, 2S*, 3S*, 5S*)-5-[5,6-Dichloro-2-(1azetidinyl)-1H-benzimidazol-1-yl]-3-(hydroxymethyl)-1,2-cyclopentanediol
(±)-(1R*, 2S*, 3R*, 5R*)-5-[5,6-Dichloro-2-(cyclopropylamino)-1H-benzimidazol-1-yl]-3-(hydroxymethyl)-1,2-cyclopentanediol
(±)-(1R*, 2S*, 3R*, 5S*)-5-[5,6-Dichloro-2-(cyclopropylamino)-1H-benzimidazol-1-yl]-3-methyl-1,2-cyclopentanediol
(1R, 2S, 3S, 5S)-5-[2-(tert-Butylamino)-5,6-dichloro-1H-benzimidazol-1-yl]-3-(hydroxymethyl)-1,2-cyclopentanediol
(±)-(1R*, 2S*, 3S*, 5S*)-5-[2-(tert-Butylamino)-5,6-dichloro-1H-benzimidazol-1-yl]-3-(hydroxymethyl)-1,2-cyclopentanediol
(±)-(1R*, 2S*, 3 S*, 5S*)-5-[5,6-Dichloro-2-(isopropylamino)-1H-benzimidazol-1-yl]-3-(hydroxymethyl)-1 ,2-cyclopentanediol
(1S,2R,3R,5R)-5-[-5,6-Dichloro-2-(isopropylamino)-1H-benzimidazol-1-yl]-3-(hydroxymethyl)-1,2-cyclopentanediol;
(1 S,2R,3R,5R)-5-[2-tert-butylamino)-5,6-dichloro-1H-benzimidazol-1-yl]-3-(hydroxymethyl)-1,2-cyclopentanediol;
(±)-(1R*, 2S*, 3S*, 5S*)-5-[5,6-Dichloro-2-(1-azetidinyl)-1H-benzimidazol-1-yl]-3-(hydroxymethyl)-1,2-cyclopentanediol;
(1R, 2S, 3S, 5S)-5-[5,6-Dichloro-2-(1-azetidinyl)-1H-benzimidazol-1-yl]-3-(hydroxymethyl)-1,2-cyclopentanediol; and
(1S, 2R, 3R, 5R)-5-[5,6-Dichloro-2-(1-azetidinyl-1H-benzimidazol-1-yl]]-3-(hydroxymethyl)-1,2-cyclopentanediol and pharmaceutically acceptable derivatives thereof.

9. A method for the treatment of a herpes viral infection in a subject which comprises treating the subject with a therapeutically effective amount of at least one compound of formula (I) or (I-1) (as defined in claim 1) or a pharmaceutically acceptable derivative thereof.

10. A method according to claim 9 wherein the herpes viral infection is a cytomegalovirus infection.

11. A method according to claim 9 wherein said compound is selected from (1R, 2S, 3S, 5S)-5-[5,6-Dichloro-2-(cyclopropylamino)-1H-benzimidazol-1-yl]-3-(hydroxymethyl)-1,2-cyclopentanediol (1R, 2S, 3S, 5S)-5-[5,6-Dichloro-2-(isopropylamino)-1H-benzimidazol-1-yl]-3-(hydroxymethyl)-1,2-cyclopentanediol (±)-(1R*, 2S*, 3S*, 5S*)-5-(5,6-Dichloro-2-amino-1H-benzimidazol-1-yl)-3-(hydroxymethyl)-1,2-cyclopentanediol (±)-(1R*, 2R*, 4S*)-2-(2-Cyclopropylamino-5,6-dichloro-1H-benzimidazol-1-yl)-4-(hydroxymethyl)cyclopentanol (±)-(1R*, 2S*, 3S*, 5S*)-5-[5,6-Dichloro-2-(cyclobutylamino)-8H-benzimidazol-1-yl]-3-(hydroxymethyl)-1,2-cyclopentanediol (±)-(1R*, 2S*, 3S*, 5S*)-5-[5,6-Dichloro-2-(1-azetidinyl)-1H-benzimidazol-1-yl]-3-(hydroxymethyl)-1,2-cyclopentanediol (±)-(1R*, 2S*, 3R*, 1R*)-5-[5,6-Dichloro-2-(cyclopropylamino)-1H-benzimidazol-1-yl]-3-(hydroxymethyl)-1,2-cyclopentanediol (±)-(1R*, 2S*, 3R*, 5S*)-5-[5,6-Dichloro-2-(cyclopropylamino)-1H-benzimidazol-1-yl]-3 -methyl-1,2-cyclopentanediol (1R, 2S, 3S, 5S)-5-[2-(tert-Butylamino)-5,6-dichloro-1H-benzimidazol-1-yl]-3-(hydroxymethyl)-1,2-cyclopentanediol (±)-(1R*, 2S*, 3S*, 5S*)-5-[2-(tert-Butylamino)-5,6-dichloro-1H-benzimidazol-1-yl]-3-(hydroxymethyl)-1,2-cyclopentanediol (±)-(1 R*, 2S*, 3S*, 5S*)-5-[5,6-Dichloro-2-(isopropylamino)-1H-benzimidazol-1-yl]-3-(hydroxymethyl)-1,2-cyclopentanediol (1S,²R,3R,5R)-5-[5,6-Dichloro-2-(isopropylamino)-1H-benzimidazol-1-yl]-3-(hydroxymethyl)-1,2-cyclopentanediol;

(1S,2R,3R,5R)-5-[2-tert-butylamino)-5,6-dichloro-1H-benzimidazol-1 -yl]-3-(hydroxymethyl)-1,2-cyclopentanediol;

(±)-(1R*, 2S*, 3S*, 5S*)-5-[5,6-Dichloro-2-(1-azetidinyl)-1H-benzimidazol-1-yl]-3-(hydroxymethyl)-1,2-cyclopentanediol;

(1R, 2S, 3S, 5S)-5-[5,6-Dichloro-2-(1-azetidinyl)-1H-benzimidazol-1-yl]-3-(hydroxymethyl)-1,2-cyclopentanediol; and (1S, 2R, 3R, 5R)-5-[5,6-Dichloro-2-(1-azetidinyl-1H-benzimidazol-1-yl]]-3-(hydroxymethyl)-1,2-cyclopentanediol, and pharmaceutically acceptable derivatives thereof.

12. Pharmaceutical formulations comprising at least one compound of formula (I) or (I-1) (as defined in claim 1) or a pharmaceutically acceptable derivative thereof together with at least one pharmaceutically acceptable carrier or excipient.

13. A pharmaceutical formulation according to claim 13 wherein said compound is selected from (1R, 2S, 3S, 5S)-5-[5,6-Dichloro-2-(cyclopropylamino)-1H-benzimidazol-1-yl]-3-hydroxymethyl)-1,2-cyclopentanediol (1R, 2S, 3S, 5S)-5-[5,6-Dichloro-2-(isopropylamino)-1H-benzimidazol-1-yl]-3-(hydroxymethyl)-1,2-cyclopentanediol (±)-(1R*, 2S*, 3S*, 5S*)-5-(5,6-Dichloro-2-amino-1H-benzimidazol-1-yl)-3-(hydroxymethyl)-1,2-cyclopentanediol (±)-(1R*, 2R*, 4S*)-2-(2-Cyclopropylamino-5,6-dichloro-1H-benzimidazol-1-yl)-4-(hydroxymethyl)cyclopentanol (±)-(1R*, 2S*, 3S*, 5S*)-5-[5,6-Dichloro-2-(cyclobutylamino)-1H-benzimidazol-1-yl]-3-(hydroxymethyl)-1,2-cyclopentanediol (±)-(1R*, 2S*, 3S*, 5S*)-5-[5,6-Dichloro-2-( 1-azetidinyl)-1H-benzimidazol-1-yl]-3-(hydroxymethyl)-1,2-cyclopentanediol (±)-(1R*, 2S*, 3R*, 5R*)-5-[5,6-Dichloro-2-(cyclopropylamino)-1H-benzimidazol-1-yl]-3-(hydroxymethyl)-1,2-cyclopentanediol (±)-(1R*, 2S*, 3R*, 5S*)-5-[5,6-Dichloro-2-(cyclopropylamino)-1H-benzimidazol-1-yl]-3-methyl-1,2-cyclopentanediol (1 R, 2S, 38, 5S)-5-[2-(tert-Butylamino)-5,6-dichloro-1H-benzimidazol-1-yl]-3-(hydroxymethyl)-1,2-cyclopentanediol (±)-(1R*, 2S*, 3S*, 5S*)-5-[2-(tert-Butylamino)-5,6-dichloro-1H-benzimidazol-1-yl]-3-(hydroxymethyl)-1,2-cyclopentanediol (±)-(1R*, 2S*, 3S*, 5S*)-5-[5,6-Dichloro-2-(isopropylamino)-1H-benzimidazol-1-yl]-3-(hydroxymethyl)-1,2-cyclopentanediol and pharmaceutically acceptable derivatives thereof.

14. A process for the preparation of preparation of compounds of formulae (I) and (a-1 (as defined in claim 1) alone or in combination with their mirror image enantiomers, and their pharmaceutically acceptable derivatives which comprises (A) reacting

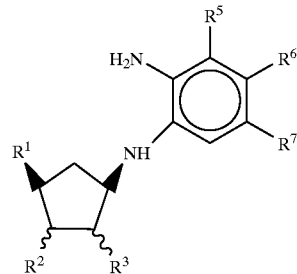

(II)

or the mirror image enantiomer thereof, with a) either a compound of formula $R^4CO_2H$ wherein $R^4$ is H, $C_{1-4}$ alkyl or $C_{1-4}$ perfluoroalkyl or a compound of formula $R^4C(OR)_3$ wherein $R^4$ is H, $C_{1-4}$ alkyl or $C_{1-4}$ perfluoroalkyl and R is $C_{1-4}$ alkyl to form a compound of formula (IA) or (IA-1) in which $R^4$ is H; or b) cyanogen bromide to form a compound of formula (IA) or (IA-1) in which $R^4$ is $NH_2$;

(B)

a) converting a compound of formula (IA) or (IA-1) in which $R^4$ is hydrogen into a farther compound of formula (IA) or (IA-1) in which $R^4$ is a leaving group; or b) converting a compound of formula (IA) or (IA-1) in which $R^4$ is Cl, Br or I into a further compound of formula (IA) or (IA-1) in which $R^4$ is an amino or substituted amino group —$NR^8R^9$ as defined above: or (C) reacting a compound of formula

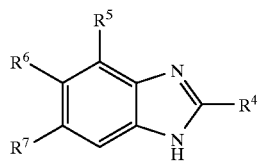
(III)

(wherein $R^4$, $R^5$, $R^6$ and $R^7$ are as herebefore defined) or a functional equivalent thereof with a compound of formula

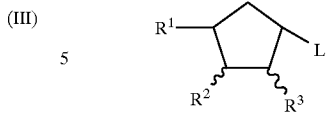
(IV)

wherein
$R^1$, $R^2$ and $R^3$ are as defined above and L is a leaving group, to form a compound of formula (IA) or (IA-1) in which $R^4$ is hydrogen, halogen or the $-NR^8R^9$ and optionally converting a compound of formula (IA) or (IA-1) into a pharmaceutically acceptable derivative thereof.

* * * * *